(12) United States Patent
Chen et al.

(10) Patent No.: US 7,091,347 B2
(45) Date of Patent: Aug. 15, 2006

(54) BICYCLIC PYRIDINE AND PYRIMIDINE P38 KINASE INHIBITORS

(75) Inventors: Jian Jeffrey Chen, Newbury Park, CA (US); Nolan James Dewdney, San Jose, CA (US); Christoph Martin Stahl, Freiburg (DE)

(73) Assignee: Roche Palo Alto LLC, Palo Alto, CA (US)

( * ) Notice: Subject to any disclaimer, the term of this patent is extended or adjusted under 35 U.S.C. 154(b) by 44 days.

(21) Appl. No.: 10/383,392

(22) Filed: Mar. 6, 2003

(65) Prior Publication Data

US 2003/0207900 A1 Nov. 6, 2003

Related U.S. Application Data

(60) Provisional application No. 60/430,508, filed on Dec. 3, 2002, provisional application No. 60/362,373, filed on Mar. 7, 2002.

(51) Int. Cl.
*C07D 491/00* (2006.01)

(52) U.S. Cl. .................. 544/278; 544/280; 514/260.1; 514/265.1

(58) Field of Classification Search ................ 544/278, 544/280; 546/114, 115, 116, 118; 514/260.1, 514/265.1, 301, 302, 303
See application file for complete search history.

(56) References Cited

U.S. PATENT DOCUMENTS

| 4,835,157 A | * | 5/1989 | Press et al. ............... 514/260.1 |
| 2001/0020030 A1 | | 9/2001 | Stewart et al. | |

FOREIGN PATENT DOCUMENTS

| WO | WO 95/29897 A1 | 11/1995 |
| WO | WO 95/33748 A1 | 12/1995 |
| WO | WO 95/33752 A1 | 12/1995 |
| WO | WO 98/01428 A1 | 1/1998 |
| WO | WO 98/08382 A1 | 3/1998 |
| WO | WO 00/39108 A1 | 7/2000 |
| WO | WO 00/43394 A1 | 7/2000 |
| WO | WO 01/49688 A | 7/2001 |
| WO | WO 02/14317 A2 | 2/2002 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
J. W. Fijen*, J. G. Zijlstra*, P. De Boer, R. Spanjersberg*, J. W. Cohen Tervaert , T. S. Van Der Werf*, J. J. M. Ligtenberg* & J. E. Tulleken*, Clinical & Experimental Immunology vol. 124 Issue 1 pp. 16—Apr. 2001.*
Hommes D, van den Blink B, Plasse T, Bartelsman J, Xu C, Macpherson B, Tytgat G, Peppelenbosch M, Van Deventer S., Gastroenterology. Jan. 2002;122(1):7-14..PMID: abstract 11781274.*
Hashimoto S, Gon Y, Matsumoto K, Maruoka S, Takeshita I, Hayashi S, Asai Y, Jibiki I, Machino T, Horie T., J Pharmacol Exp Ther. May 2000;293(2):370-5.*
Hurst, Derek T. An Introduction to the Chemistry and Biochemistry of the Pyrimidines, Purines, and Pteridines, London: John Wiley and Sons. 1980 pp. 26-27.*
Ganghyeok Kim et al, "Design, Synthesis, and Evaluation of 1,5-Disu",Array Biopharma, [online] no date [retrieved on Apr. 28, 2005]. Retrieved from the Internet, <http://media. corporate-ir.net/media_files/nsd/arry/posters/0304ACS-Anaheim-Poster.pdf>.*
Michael Greer, "HIV/AIDS Dementia: CPI-1189 safe but ineffective", AIDSWEEKLY Plus; [online] AIDSWEEKLY Plus; Monday, Jan. 20, 2003 [retrieved on Apr. 28, 2005]. Retrieved from the Internet, <http://www.aegis.com/pubs/aidswkly/2003/AW030107.html>.*
Henry, James R., et al., "6-Amino-2-(4-fluorophenyl)-4-methoxy-3-(4-pyridyl)-1H-pyrrolo[2,3-b]pyridine (RWJ 68354): A Potent and Selective p38 Kinase Inhibitor", *J. Med. Chem*, 1998, 41: 4196-4198.
Koch, A., et al., "Effect of smoking on MAP kinase-induced modulation of IL-8 in human alveolar macrophages", *Eur. Respir. J.*, 2004, 23: 805-812.
Noble, Martin E. M., et al., "Protein Kinase Inhibitors: Insights into Drug Design from Structure", Science, 2004, 303: 1800-1804.
Trejo, Alejandra, et al., "Design and Synthesis of 4-Azaindoles as Inhibitors of p38 MAP Kinase", *J. Med. Chem.*, 2003, 46: 4702-4713.

* cited by examiner

Primary Examiner—Thomas C. McKenzie
(74) Attorney, Agent, or Firm—Grant D. Green

(57) ABSTRACT

The present invention discloses compounds corresponding to formula

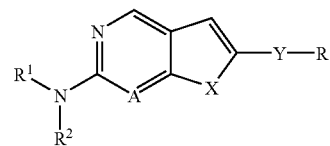

wherein A, R, X, Y, R, $R^1$ and $R^2$ are as defined above, pharmaceutical formulations, methods of making and uses thereof.

8 Claims, No Drawings

BICYCLIC PYRIDINE AND PYRIMIDINE P38 KINASE INHIBITORS

CROSS REFERENCE TO RELATED INVENTIONS

This application claims the priority benefit under Title 35 U.S.C. 119(e) of U.S. Provisional Applications Ser. No. 60/362,373, filed on Mar. 7, 2002 and Ser. No. 60/430,508, filed Dec. 3, 2002, the disclosures of which are herein incorporated by reference in their entirety.

FIELD OF THE INVENTION

The present invention relates to certain bicyclic pyridine and pyrimidine derivatives as p38 protein kinase inhibitors. In particular, the present invention relates to 2-substituted amino-bicyclic pyridine and pyrimidine compounds, a process for their manufacture, pharmaceutical preparations comprising the same, and methods for using the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group which includes various isoforms (e.g., p38α, p39β, p38γ and p38δ). The p38 kinases are responsible for phosphorylating and activating transcription factors as well as other kinases, and are themselves activated by physical and chemical stress, pro-inflammatory cytokines and bacterial lipopolysaccharide.

More importantly, the products of the p38 phosphorylation have been shown to mediate the production of inflammatory cytokines, including TNF, IL-1 and IL-6, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, Alzheimer's disease, Crohn's disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpes virus-7 (HHV-7), human herpes virus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

The inhibition of these cytokines by inhibition of the p38 kinase is of benefit in controlling, reducing and alleviating many of these disease states.

SUMMARY OF THE INVENTION

One aspect of the present invention provides compounds represented by the formula:

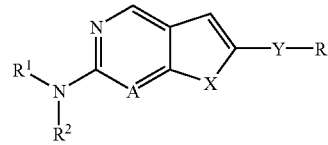

wherein:
A is N or CH;
$R^1$ is hydrogen, alkyl or aralkyl;
$R^2$ is alkyl, heteroalkyl, $(R'')_2$NCO-alkylene-(where each R" is independently hydrogen or alkyl), cycloalkyl, heterocyclyl, aryl, or heteroaryl;
X is O, $N(R^3)$ or S, wherein $R^3$ is hydrogen, alkyl or aryl;
Y is a bond, O, N(R'), C(=O), CH(OR'), CHR', or S(O)$_n$, wherein n is 0, 1, or 2; and R' is hydrogen or alkyl; and
R is aryl or heteroaryl; and isomers, pharmaceutically acceptable salts, esters or prodrugs thereof.

The compounds of formula I and their pharmaceutically acceptable salts are inhibitors of protein kinases and exhibit effective activity against p38 in vivo. Therefore, the compounds can be used for the treatment of diseases mediated by the pro-inflammatory cytokines such as TNF and IL-1.

Thus, in another aspect, the present invention relates to methods for the treatment of p38 mediated diseases or conditions in which a therapeutically effective amount of a compound of formula I is administered to a patient in need of such treatment.

In yet another aspect, the present invention relates to methods for preparing the compounds described above.

In yet still another aspect, the present invention relates to methods for preparing medicaments useful for the treatment of the p38 mediated diseases and conditions.

In yet another aspect of the invention, there are provided compounds useful as intermediates in preparing compounds of formula (I).

Definitions

As used herein, the term "alkyl" means a linear or branched saturated monovalent hydrocarbon moiety of one to six carbon atoms, e.g., methyl, ethyl, n-propyl, 2-propyl, tert-butyl, pentyl, and the like."Alkylene" means a linear or branched saturated divalent hydrocarbon moiety of one to six carbon atoms, e.g., methylene, ethylene, propylene, and the like.

The term "aryl" refers to a monovalent monocyclic or bicyclic aromatic hydrocarbon moiety which is optionally substituted independently with one or more, preferably one, two or three, substituents. Preferably, each substituent is independently selected from the group consisting of alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl, —Y-heterocyclyl, —Y—OR$^p$, —Y—NR$^p$R$^q$, —Y—C(O)—R$^p$, —YS(O)$_{0-2}$R$^p$, —Y—N—S(O)$_2$R$^p$, —Y—S(O)$_2$NR$^p$R$^q$, —Y—N—C(O)NR$^p$R$^q$, where Y is absent or a $C_1$–$C_3$ alkylene group, and R$^p$ and R$^q$ are independently selected from hydrogen, alkyl, haloalkyl, hydroxy, alkoxy, aryl, heteroaryl, cycloalkyl, and heterocyclyl, except when said substituent is —YS(O)$_{1-2}$R$^p$ or —Y—N—S(O)$_2$R$^p$, then R$^p$ in these instances is not hydrogen. A particularly preferred group of aryl substituents are those selected from alkyl, haloalkyl, halo, hydroxy, amino, haloalkoxy and heteroalkyl. Within this group of aryl substituents, halide, alkyl and alkoxy are especially preferred. More specifically the term aryl includes, but is not limited to, phenyl, chlorophenyl, methoxyphenyl, 1-naphthyl, 2-naphthyl, and the derivatives thereof.

"Aralkyl" means a moiety of the formula —$R^xR^y$ where $R^x$ is an alkylene group and $R^y$ is an aryl group as defined above. Exemplary aralkyls include benzyl, phenylethylene, and the like.

The term "cycloalkyl" as used herein refers to a saturated monovalent cyclic hydrocarbon moiety of three to seven ring carbons, e.g., cyclopentyl, cyclobutyl, cyclohexyl, and the like. Cycloalkyl may optionally be substituted with one, two or three substituents. Preferably, each substituent is independently selected from the group consisting of alkyl, hydroxy, alkoxy, amino, monosubstituted amino, disubstituted amino, haloalkyl, halo, cyanoalkyl, oxo (i.e., carbonyl oxygen), heteroalkyl, heterocyclyl, hydroxyalkyl, and —$(X)_n$—C(O)R' (where, X is O or NR", n is 0 or 1, R" is hydrogen, alkyl, haloalkyl, amino, monosubstituted amino, disubstituted amino, hydroxy, alkoxy, alkyl or optionally substituted phenyl, and R' is H or alkyl), and —$S(O)_nR'$ (wherein n is 0 to 2 provided where n is 1 or 2, R' is not hydrogen). A particularly preferred group of cycloalkyl substituents are those selected from alkyl, hydroxy, alkoxy, amino, monosubstituted amino, disubstituted amino, haloalkyl and halo. Among this group of cycloalkyl substituents, alkyl, hydroxy, alkoxy, haloalkyl and halo are especially preferred. More specifically, the term cycloalkyl includes cyclopentyl, cyclohexyl, 4-hydroxycyclohexyl, and the like.

The term "halo," "halide" or "halogen," when referring to a substituent means fluoro, chloro, bromo, or iodo.

The term "haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all alkyl hydrogen atoms are replaced by fluorine atoms.

The term "heteroalkyl" as used herein means an alkyl moiety defined above, wherein one, two or three hydrogen atoms have been replaced with a substituent independently selected from the group consisting of —$OR^a$, —$NR^bR^c$, and $S(O)_nR^d$ (where n is an integer from 0 to 2), with the understanding that the point of attachment of the heteroalkyl moiety is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; or $R^b$ and $R^c$ together with the nitrogen atom to which they are attached form heterocyclyl or heteroaryl; and when n is 0, $R^d$ is hydrogen, akyl, cycloalkyl, or cycloalkylalkyl, and when n is 1 or 2, $R^d$ is alkyl, cylcoalkyl, cycloalkylalkyl, amino, acylamino, monoalkylamino, or dialkylamino. Representative examples include, but are not limited to, 2-hydroxyethyl, 3-hydroxypropyl, 2-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, methylaminosulfonylmethyl, methylaminosulfonylethyl, methylaminosulfonylpropyl, and the like. When $R^a$ in the moiety—$OR^a$ is hydrogen, "heteroalkyl" is also referred to as "hydroxyalkyl" and includes, but is not limited to, 2-hydroxyethyl, 3-hydroxypropyl, 2-hydroxymethylethyl, 2,3-dihydroxypropyl, 1-hydroxymethylethyl, 3-hydroxybutyl, 2,3-dihydroxybutyl, and 2-hydroxy-1-methylpropyl. "Monosubstituted amino" means a moiety —$NHR^e$ where $R^e$ is alkyl, heteroalkyl, haloalkyl, cycloalkyl, cycloalkylalkyl, hydroxyalkyl, aryl, aralkyl, aralkenyl, heteroaryl, heteroalkyl, heteroaralkenyl, heterocyclyl, or heterocyclylalkyl, e.g., methylamino, ethylamino, phenylamine, benzylamine, and the like. Similarly, the term "disubstituted amino" refers to a moiety —$NR^gR^h$ wherein $R^g$ and $R^h$ are, independently of each other, alkyl, heteroalkyl, haloalkyl, cycloalkyl, cycloalkylalkyl, hydroxyalkyl, aryl, aralkyl, aralkenyl, heteroaryl, heteroalkyl, heteroaralkenyl, heterocyclyl, or heterocyclylalkyl, or $R^g$ and $R^h$ together with the nitrogen atom to which they are attached form a heterocyclyl ring. Representative examples include, but are not limited to, dimethylamino, methylethylamino, di(1-methyl-ethyl)amino, piperazinyl, piperdinyl and the like.

"Heterocyclyl" means a saturated or partially-unsaturated non-aromatic cyclic moiety in which one or two ring atoms are heteroatoms selected from N, O, or $S(O)_n$ (where n is an integer from 0 to 2), the remaining ring atoms being C, where one or two C atoms may optionally contain a carbonyl oxygen group, e.g., one or two atoms in the ring may be a moiety of the formula —C(=O)—. The heterocyclyl ring may be optionally substituted independently with one, two, or three substituents selected from alkyl, hydroxy, hydroxyalkyl, alkoxy, heteroalkyl, and haloalkyl. More specifically the term heterocyclyl includes, but is not limited to, tetrahydropyranyl, piperidinyl, piperazinyl, morpholinyl, and the like.

"Heteroaryl" means a monovalent monocyclic or bicyclic aromatic moiety of 5 to 12 ring atoms containing one, two, or three ring heteroatoms each independently selected from N, O, or S, the remaining ring atoms being C. The heteroaryl ring can optionally be substituted with one or more substituents, preferably one or two substituents, each substituent being independently selected from alkyl, haloalkyl, heteroalkyl, heterocyclyl, halo, nitro, cyano, carboxy, acyl, -(alkylene)$_n$—COOR (where n is 0 or 1 and R is hydrogen, alkyl, optionally substituted phenylalkyl, or optionally substituted heteroaralkyl), or -(alkylene)$_n$—$CONR^aR^b$ (where n is 0 or 1, and $R^a$ and $R^b$ are, independently of each other, hydrogen, alkyl, cycloalkyl, cycloalkylalkyl, hydroxyalkyl, aryl, or $R^a$ and $R^b$ together with the nitrogen atom to which they are attached form a heterocyclyl or heteroaryl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuranyl, and benzodiazepin-2-one-5-yl, and the derivatives thereof.

The term "acyl" refers to the group —C(O)R' where R' is alkyl, haloalkyl, heteroalkyl, aryl, heteroaryl, aralkyl or heteroaralkyl.

"Alkoxy", "aryloxy", "aralkyloxy", or "heteroaralkyloxy" means a moiety —OR where R is an alkyl, aryl, aralkyl, or heteroaralkyl, respectively, as defined above e.g., methoxy, phenoxy, pyridin-2-ylmethyloxy, benzyloxy, and the like.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a grouping of atoms that when attached to a reactive group in a molecule masks, reduces or prevents that reactivity. Examples of protecting groups can be found in T. W. Green and P. G. Wuts, *Protective Groups in Organic Chemistry*, (Wiley, 2nd ed. 1991) and Harrison and Harrison et al., *Compendium of Synthetic Organic Methods*, Vols. 1–8 (John Wiley and Sons, 1971–1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

DETAILED DESCRIPTION OF THE INVENTION

In one embodiment, the present invention provides compounds represented by the formula:

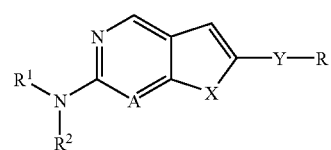

I wherein A, $R^1$, $R^2$, X, Y and R are as defined above.

Some of the representative compounds of formula I are shown in Table 1 below.

TABLE 1

Compounds of formula I, wherein the values of $R^1$, $R^2$, $R^3$, R', A, X, Y and R are set forth below:

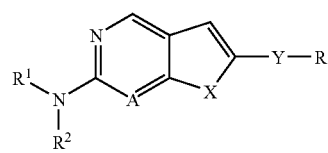

I

| Cpd. # | $R^1$ | $R^2$ | R' | $R^3$ | A | X | Y | R | MP° C. | MS M + H |
|---|---|---|---|---|---|---|---|---|---|---|
| 1 | H | 4-hydroxy-cyclohexyl | — | — | N | S | CO | phenyl | 102.6–103.8 | 354 |
| 2 | H | N-methylsulfonylpiperidin-4-yl | — | — | N | S | CO | phenyl | 216.3–217.6 | 417 |

TABLE 1-continued

Compounds of formula I, wherein the values of $R^1$, $R^2$, $R^3$, R', A, X, Y and R are set forth below:

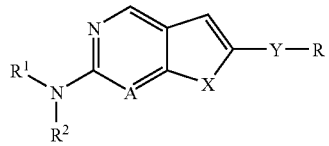

I

| Cpd. # | $R^1$ | $R^2$ | R' | $R^3$ | A | X | Y | R | MP° C. | MS M + H |
|---|---|---|---|---|---|---|---|---|---|---|
| 3 | H | tetrahydropyran-4-yl | — | — | N | S | CO | phenyl | 219.5–220.5 | 340 |
| 4 | H | tetrahydropyran-4-yl | — | — | N | S | CO | 4-fluorophenyl | 236–238.7 | 358 |
| 5 | H | tetrahydropyran-4-yl | — | — | N | S | CO | 2-chlorophenyl | — | — |
| 6 | H | N-methylsulfonylpiperidin-4-yl | — | — | N | S | CO | 2-fluorophenyl | 213.3–216.1 | 435 |
| 7 | H | N-methylsulfonylpiperidin-4-yl | — | — | N | S | CO | 3-fluorophenyl | 225.4–225.7 | 435 |
| 8 | H | tetrahydropyran-4-yl | — | — | N | S | CO | 3-fluorophenyl | 186.7–188.8 | 358 |
| 9 | H | tetrahydropyran-4-yl | — | — | N | S | CO | 2-fluorphenyl | 195.2–195.5 | 358 |
| 10 | H | (1,1-dimethyl-2-hydroxy)ethyl | — | — | N | S | CO | 2-fluorphenyl | 105-108.5 | 346 |
| 11 | H | tetrahydropyran-4-yl | — | — | N | S | CO | 4-chlorophenyl | 261.4–262.9 | 374 |
| 12 | H | N-methylsulfonylpiperidin-4-yl | — | — | N | S | CO | 4-fluorophenyl | 250.3–251.1 | 435 |
| 13 | H | N-methylsulfonylpiperidin-4-yl | — | — | N | S | CO | 4-chlorophenyl | 260.8–261.8 | — |
| 14 | H | N-methylsulfonylpiperidin-4-yl | — | — | N | S | CO | 2-chlorophenyl | 188.1–188.5 | 451 |
| 15 | H | 1,1-dioxo-tetrahydrothiopyran-4-yl (See cpd. #36) | — | — | N | S | CO | 2-fluorophenyl | 217.9–221.8 | 406 |
| 16 | H | N-methylsulfonylpiperidin-4-yl | — | — | N | S | CO | 3-fluorophenyl | 191–193.4 | 406 |
| 17 | H | (1,1-dimethyl-2-hydroxy)ethyl | — | — | N | S | CO | 3-fluorophenyl | 133.3–134.6 | 346.1 |
| 18 | H | (1-methyl-2-methoxy)ethyl | — | — | N | S | CO | 3-fluorophenyl | 159.4–167.2 | 346 |
| 19 | H | (1-methyl-2-hydroxy)ethyl | — | — | N | S | CO | 3-fluorophenyl | 148.6–150.5 | 332 |
| 20 | H | (1-methyl-2,2-dimethyl-2-hydroxy)ethyl | — | — | N | S | CO | 2-chlorophenyl | 106–113 | 376 |
| 21 | H | 1-(2,2-dimethyl-2-hydroxyethyl)ethyl | — | — | N | S | CO | 2-fluorophenyl | 104.4–117.3 | 360 |
| 22 | H | N-methylsulfonylpiperidin-4-yl | H | — | N | S | $CH_2$ | phenyl | 215–217 | 403 |
| 23 | H | N-methylsulfonylpiperidin-4-yl | H | — | N | S | CHOH | phenyl | 152.2–162.1 | 419 |
| 24 | H | tetrahydropyran-4-yl | H | — | N | S | CHOH | 2-fluorophenyl | — | 360.2 |
| 25 | H | tetrahydropyran-4-yl | H | — | N | S | $CH_2$ | 2-fluorophenyl | 217–219 | 344 |
| 26 | H | tetrahydropyran-4-yl | — | — | N | S | CO | 2-methyl-phenyl | 183–188 | 354 |
| 27 | H | tetrahydropyran-4-yl | — | — | N | S | CO | 2-methoxy-phenyl | 194.4–198.4 | 370 |
| 28 | H | tetrahydropyran-4-yl | — | — | N | S | CO | 3-methoxy-phenyl | 206–208.6 | 370 |
| 29 | H | tetrahydropyran-4-yl | H | — | N | O | $CH_2$ | phenyl | — | 310.3 |
| 30 | H | cyclopentyl | H | — | N | O | $CH_2$ | phenyl | — | 294.2 |
| 31 | H | 4-hydroxycyclohexyl | H | — | N | O | $CH_2$ | phenyl | — | 324.2 |
| 32 | H | tetrahydropyran-4-yl | — | methyl | N | N | CO | 2-methoxy-phenyl | — | 367.2 |
| 33 | H | cyclopentyl | H | methyl | N | N | $CH_2$ | phenyl | — | 307.3 |
| 34 | H | 4-hydroxycyclohexyl | H | methyl | N | N | $CH_2$ | phenyl | — | 337.2 |
| 35 | H | tetrahydropyran-4-yl | H | methyl | N | N | $CH_2$ | phenyl | — | 323.2 |

TABLE 1-continued

Compounds of formula I, wherein the values of $R^1$, $R^2$, $R^3$, R', A, X, Y and R are set forth below:

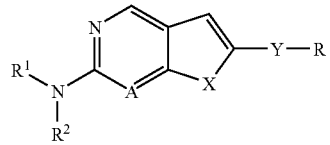

I

| Cpd. # | $R^1$ | $R^2$ | R' | $R^3$ | A | X | Y | R | MP° C. | MS M + H |
|---|---|---|---|---|---|---|---|---|---|---|
| 36 | H | 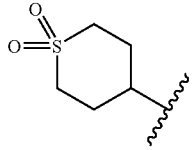 (i.e., 1,1-dioxo-tetrahydrothiopyran-4-yl) | — | — | N | S | CO | 4-fluorophenyl | >300 | 406 |
| 37 | H | tetrahydropyran-4-yl | — | — | N | O | — | phenyl | 224–226 | 296 |
| 38 | H | isopropyl | — | — | N | O | $CH_2$ | phenyl | | 268.2 |
| 39 | H | phenyl | — | phenyl | N | N | — | 4-methoxyphenyl | | |
| 40 | H | 1-(2-hydroxyethyl)-3-hydroxypropyl | — | — | N | S | CO | 2-methoxyphenyl | | 388 |
| 41 | H | tetrahydropyran-4-yl | — | — | N | S | S | 2,4-difluorophenyl | | 380 |
| 42 | H | tetrahydropyran-4-yl | — | — | N | S | O | 2,4-difluorophenyl | | 364 |
| 43 | H | tetrahydropyran-4-yl | — | — | N | S | S | phenyl | | 344 |

In one preferred group of compounds of Formula I, R is aryl. Preferred aryl groups are optionally substituted phenyl. Particularly preferred optionally substituted phenyls are phenyl (i.e., non-substituted phenyl), mono- and di-halo substituted phenyls, alkylsubstituted phenyls, and alkoxysubstituted phenyl. Especially preferred optionally substituted phenyls are phenyl, 4-fluorophenyl, 2-chlorophenyl, 2-fluorophenyl, 3-fluorophenyl, 4-chlorophenyl, 2-methoxyphenyl, 2-methylphenyl, 3-methoxyphenyl, 4-methoxyphenyl, and 2,4-difluorophenyl.

In another preferred group of compounds of Formula I, Y is C(=O), $CH_2$, CH(OH), a bond (i.e., absent), S or O.

Yet in another preferred group of compounds of Formula I, A is N.

Still in another preferred group of compounds of Formula I, $R^1$ is hydrogen.

Yet in another preferred group of compounds of Formula I, $R^2$ is heterocyclyl, cycloalkyl, heteroalkyl, alkyl, or aryl. Within this group of $R^2$, 4-hydroxycyclohexyl, N-methylsulfonylpiperidin-4-yl, tetrahydropyran-4-yl, (1,1-dimethyl-2-hydroxy)ethyl, 1,1-dioxo-tetrahydrothiopyran-4-yl, 2-methoxy-1-methylethyl, 2-hydroxy-1-methylethyl, 1,2-dimethyl-2-hydroxypropyl, cyclopentyl, isopropyl, phenyl, and 1-(2-hydroxyethyl)-3-hydroxypropyl are particularly preferred.

Still further, combinations of the preferred groups described herein form other preferred embodiments. In this manner, a variety of preferred compounds are embodied within the present invention. Representative groups of particularly preferred compounds are described below.

One preferred group of compounds of formula I are those wherein Y is $CH_2$ or C(=O); and R is a phenyl optionally substituted with a hydrogen, halogen, methyl, trifluoromethyl, alkoxy, trifluoromethoxy, cyano, nitro or amino.

More preferred compounds in this embodiment are compounds of formula I, wherein A is N, Y is $CH_2$ or C(=O), and X is S. Still more preferred compounds are compounds of formula I wherein A is N, Y is C(=O), $R^1$ is hydrogen and $R^2$ is a cycloalkyl, heterocycloalkyl or an aryl.

Particularly preferred compounds of formula I are those wherein A is N, X is S, Y is C(=O) and R is a phenyl optionally substituted with halogen, alkyl, trifluoromethyl, alkoxy or hydroxyalkyl, $R^1$ is hydrogen and $R^2$ is a cycloalkyl, heterocycloalkyl or an aryl.

Most preferred compounds are those of formula I wherein A is N, X is S, Y is C(=O), R is phenyl substituted with halogen, alkyl, trifluoromethyl, alkoxy or hydroxyalkyl, $R^1$ is hydrogen and $R^2$ is a heterocyclyl group.

In another preferred embodiment of compounds of Formula I, Y is O or S. Within this group of compounds of Formula I, preferably A is N. More preferred compounds within this group are those where X is S. In particular, compounds where $R^2$ is heterocyclyl are still more preferred. Still further preferred compounds within this group are those where R is aryl, in particular where R is optionally substituted phenyl. More particularly, those compounds where $R^1$ is hydrogen are especially preferred.

Still in another preferred embodiment of compounds of Formula I, Y is a bond, i.e., R is directly attached to the core heteroaryl group on the carbon atom adjacent to the X moiety. Particularly preferred compounds within this embodiment are those where X is O or $NR^3$. Still more preferred are those where $R^2$ is heterocyclyl or aryl. One specific group of compounds within this group are those where $R^3$ is phenyl.

Yet in another preferred embodiment of compounds of Formula I, R is aryl, preferably optionally substituted phenyl. Particularly preferred are those where A is N. More preferred compounds within this group of compounds of Formula I are those where $R^1$ is hydrogen. Still more preferred compounds are those where $R^2$ is alkyl, hydroxyalkyl, cycloalkyl, heterocyclyl or aryl, with those where $R^3$ is methyl or phenyl being especially preferred.

In yet another preferred embodiment of compounds of Formula I, A is N. Preferred compounds within this group are those where R is aryl, with compounds where $R^2$ is alkyl, hydroxyalkyl, cycloalkyl, heterocyclyl or aryl being particularly preferred. Especially preferred are those where $R^1$ is hydrogen.

The compounds of the present invention can exist in unsolvated forms as well as solvated forms, including hydrated forms and all such forms are intended to be encompassed within the scope of the invention. Furthermore, as stated above, the present invention also includes all pharmaceutically acceptable salts of the compounds along with prodrug forms of the compounds and all stereoisomers whether in a pure chiral form, a racemic mixture, or enantiomeric mixture form.

The compounds of formula I are capable of further forming pharmaceutically acceptable acid addition salts. As stated above, all of these forms are also contemplated within the scope of the claimed invention.

Pharmaceutically acceptable acid addition salts of the compounds of formula I include salts derived from inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, pthalate, benzenesulfonate, toluenesulfonate, phenylacetate, citrate, lactate, maleate, tartarate, methanesulfonate, and the like. Also contemplated are salts of amino acids such as arginate and the like and gluconate, galacturonate (see, for example, Berge et al., "Pharmaceutical Salts," *J. of Pharmaceutical Science*, 1977, 66, 1–19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms somewhat in certain physical properties such as solubility in polar solvents, but otherwise the salts are equivalent to their respective free base for the purposes of the present invention.

Pharmaceutically acceptable base addition salts can be formed with metal ions or amines, such as alkali and alkaline earth metal ions or organic amines. Examples of metal ions which are used as cations include sodium, potassium, magnesium, calcium, and the like. Examples of suitable amines are N,N'-dibenzylethylenediamine, chlororocaine, choline, diethanolamine, ethylenediamine, N-methylglucamine, and procaine (see, for example, Berge et a., supra).

The base addition salts of acidic compounds can be prepared by contacting the free acid form with a sufficient amount of the desired base to produce the salt in the conventional manner. The free acid form can be regenerated by contacting the salt form with an acid and isolating the free acid in the conventional manner. The free acid forms may differ from their respective salt forms somewhat in certain physical properties such as solubility in polar solvents, but otherwise the salts are equivalent to their respective free acid for the purposes of the present invention.

All patents, patent applications and publications cited in this application are hereby incorporated by reference in their entirety for all purposes to the same extent as if each individual patent, patent application or publication were so individually denoted.

Processes for Preparing the Compounds

The compounds of the present invention can be prepared by a variety of methods, using procedures well-known to those of skill in the art. The following schemes illustrate the processes of making the compounds of the invention.

Abbreviations

The abbreviations used herein have the following meaning:

MCPBA: m-chloroperbenzoic acid.

NMP: N-methylpyrrolidine.

THF: tetrahydrofuran.

TLC: thin layer chromatography.

EtOAc: ethyl acetate.

Scheme 1

Scheme 1 describes the method of preparing a compound of formula I(a) and its analogs I(b) and I(c).

Treatment of a compound of formula 1 with potassium fluoride provides a compound of formula 2, which is then converted to a carboxaldehyde 3 according to the literature procedure (Ple, N.; Turck, A.; Heynderickx, A.; Queguiner, G. J.; *Heterocyclic Chem*. 1994, 31, 1311). Carboxaldehyde 3 can be coupled with the substituted phenacylthiols without further purification to give a compound of formula formula 4. The reaction is typically carried out with triethylamine as the base at about 0° C. to about room temperature.

Oxidation of compound 4 with an oxidizing agent, such as 3-chloroperbenzoic acid (i.e., MCPBA) or Oxone®, provides a sulfone 5 which can be converted into a variety of target compounds. Typically the oxidation of 5 is carried out in a solvent which is inert under the conditions of the oxidation. For example, when MCPBA is used as the oxidizing agent, the solvent is preferably a halogenated aliphatic hydrocarbon, especially dichloromethane.

When Oxone® is used an the oxidizing agent, the solvent is typically a mixture of water and tetrahydrofuran. The reaction temperature depends on the solvent used. For an organic solvent, the reaction temperature is generally at about –20° C. to about 50° C., preferably about 0° C. to about room temperature. When water is used as the solvent, the reaction temperature is generally from about 0° C. to about 50° C., preferably about 0° C. to about room temperature.

Reaction of compound 5 with an amine of formula $R^1R^2NH$, where $R^1$ and $R^2$ are as defined above, affords a compound of formula I(a). The reaction can be carried out in the presence or absence of a solvent. Conveniently, the reaction is carried out at temperatures of from about 0° C. to about 200° C., more preferably about room temperature to about 150° C.

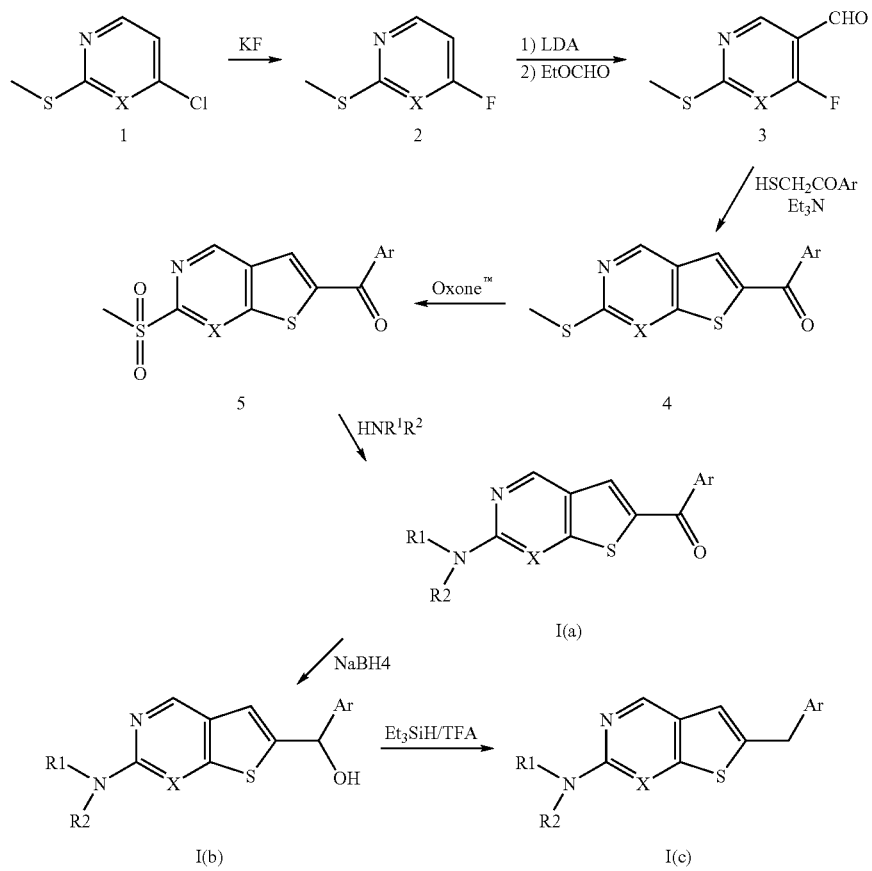

Compound I(a) can be reduced to the alcohol of formula I(b) by carrying out the reduction with a reducing agent, such as sodium borohydride in ethanol at room temperature. Compound of formula I(b) can in turn be converted to a compound of formula I(c). This reduction is usually carried out in dichloromethane with triethylsilane and trifluoroacetic acid.

Alternatively (not shown here), reaction of compound 5 with ammonia provides a compound of formula I(a)' (i.e., compound of formula I, where $R^1$ and $R^2$ are hydrogen). Further alkylation of I(a)' then provides compounds of formula I, where $R^1$ and/or $R^2$ are not hydrogen. The reaction can be carried out in the presence or absence of solvent. Conveniently, the reaction is carried out at temperatures of from about 0° C. to about 200° C., more preferably about room temperature to about 150° C. Alternatively (not shown here), in some cases rather than using the sulfone 5, the sulfide 4 can be reacted directly with an amine ($R^1R^2NH$) to provide the compounds of formula I(a).

Scheme 2

Scheme 2 illustrates a method of preparing the pyrrole analog of compound I(a). The condensation of the amino aldehyde 6 with a substituted phenacyl bromide gives compound 7. The reaction is typically carried out in NMP at 80° C. Compound 7 is then oxidized to sulfone 8 by the method described above under Scheme 1. Sulfone 8 is then reacted with an appropriate amine as described above to afford compound of formula II.

Scheme 2

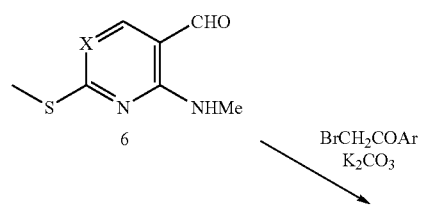

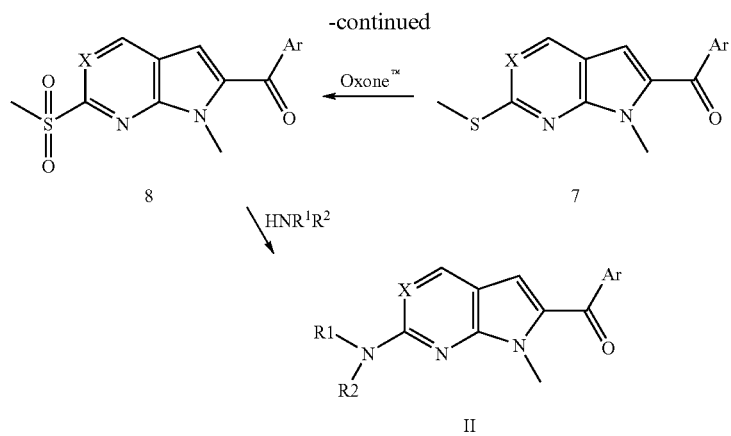

Scheme 3

A furan analog of compound of formula I(a) can be prepared according to Scheme 3. A compound 8 (prepared according to methods described in Sakamoto, T.; Kondo, Y.; Watanabe, R.; Yamanaka, H.; *Chem. Pharm. Bull.* 1986, 34, 2719) can be converted to a compound 9 by palladium catalyzed coupling with alkynes and cyclization (see: Sakamoto, T.; Kondo, Y.; Watanabe, R.; Yamanaka, H.; *Chem. Pharm. Bull.* 1986, 34, 2719). Compound 9 is then oxidized to a compound 10 by methods described above. Compound 10 is then reacted with a desirable amine of formula HNR$^1$R$^2$ to afford a compound of formula III.

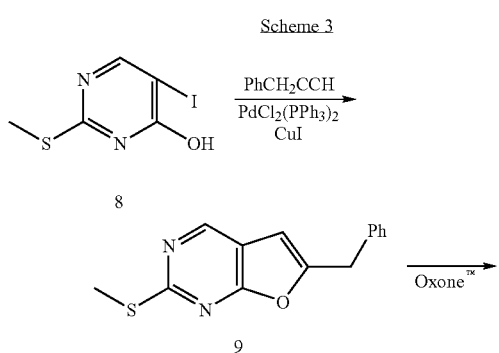

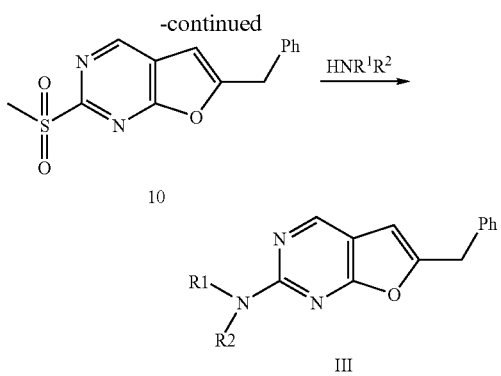

Scheme 3A

Alternatively, compound 8 can be converted into a silyl furanopyrimidine of formula 11 which can be coupled with aryl aldehyde to give an alcohol of formula 12 by the procedure described in the literature. (Aquila, B. M;. *Tetrahedron Lett.* 1997, 38, 2795). Compound 12 is then converted into a sulfone 13 which can then be converted to a compound of formula III (a) by reaction with an amine of formula HNR$^1$R$^2$. Compound III(a) is then converted into other derivatives thereof as described above in Scheme 1 and also by a number of routes available to those skilled in the art.

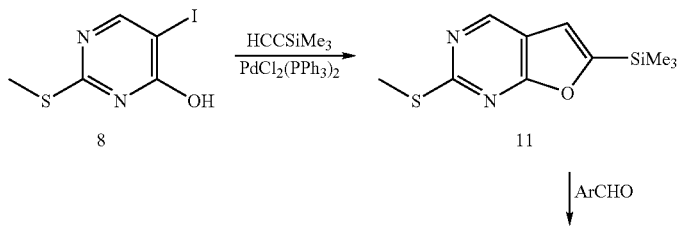

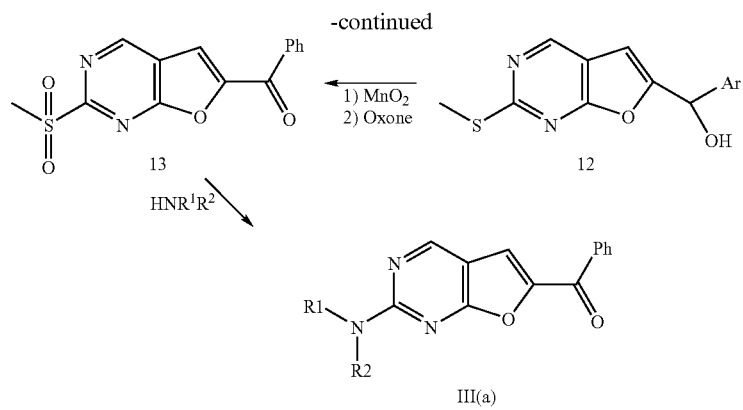

Scheme 4

A compound of formula IV can be prepared according to Scheme 4. A compound of formula 14 (prepared according to methods described in Sakamoto, T.; Kondo, Y.; Watanabe, R.; Yamanaka, H.; *Chem. Pharm. Bull.* 1986, 34, 2719) is converted to a compound of formula 15 via a palladium catalyzed coupling reaction with an alkyne. Compound 15 is then treated with methylamine to afford compound 16. The cyclization of compound 16 to compound 17 can be accomplished by treatment with a mixture of CuI and PdCl$_2$(PPh$_3$)$_2$. Compound 17 is then converted to sulfone 18 and finally to a compound of formula IV by methods described in the previous schemes.

carbonic acid O-propyl ester of formula 5-4 to produce a thienopyrimidin-4-one of formula 5-5. Methylation of the thienopyrimidin-4-one of formula 5-5 with methyl iodide then gave a corresponding thioether of formula 5-6. Oxidation and simultaneous chlorination of the thioether of formula 5-6 is then achieved using POCl$_3$ to afford thienopyrimidine of formula 5-7. Oxidation of the thioether of formula 5-7 to a sulfonyl compound of formula 5-8 is achieved using an oxidizing agent, e.g., Oxone. The chloro-substituent on the pyrimidine ring system is then reduced by hydrogenation using palladium on carbon catalyst to afford 2-methanesulfonyl-thieno[2,3-d]pyrimidine of formula 5-9. The methanesulfonyl group of formula 5-9 can be replaced

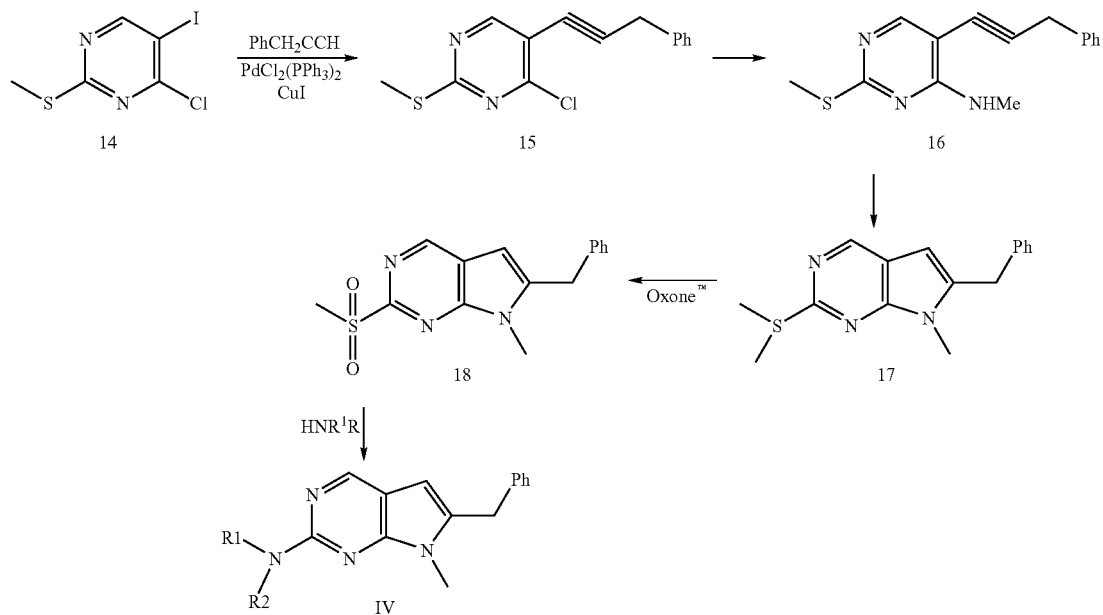

Scheme 5

Compounds of formulae Va and Vb can be prepared according to Scheme 5. A compound of formula 5-1 is reacted with α-cyanoacetamide of formula 5-2 to afford a thiophene compound of formula 5-3. The thiophene compound 5-3 is then reacted with a potassium salt of dithiowith a desired amine compound to afford a desired amino-substituent. For example, as shown in Scheme 5, the methanesulfonyl group is displaced with 4-aminotetrahydropyran of formula 5-10 to yield 2-(tetrahydropyran-4-yl)amino-substituted thienopyrimidine of formula 5-11. This thienopyrimidine of formula 5-11 is then halogenated, e.g., using mercury (II) oxide and iodine, to afford iodo-substituted thienopyrimidine of formula 5-12. The iodo-substituted thienopyrimidine of formula 5-12 can be reacted with a variety of compounds, such as phenols (e.g., compound of formula 5-13, and its corresponding thiophenol compound, not shown) and or metalated by treatment with an organometallic reagent (e.g. alkyl lithiums) and subsequent reaction with disulfides (e.g., compound of formula 5-14), to yield corresponding coupled products, e.g., compounds of formulas Va and Vb, respectively.

One of skill in the art will understand that certain modifications to the above schemes are contemplated and within the scope of the present invention. For example, certain steps will involve the use of protecting groups for functional groups that are not compatible with particular reaction conditions.

Pharmaceutical Compositions Containing the Compounds

The compounds of formula I and the pharmaceutically acceptable salts of compounds of formula I can be used as

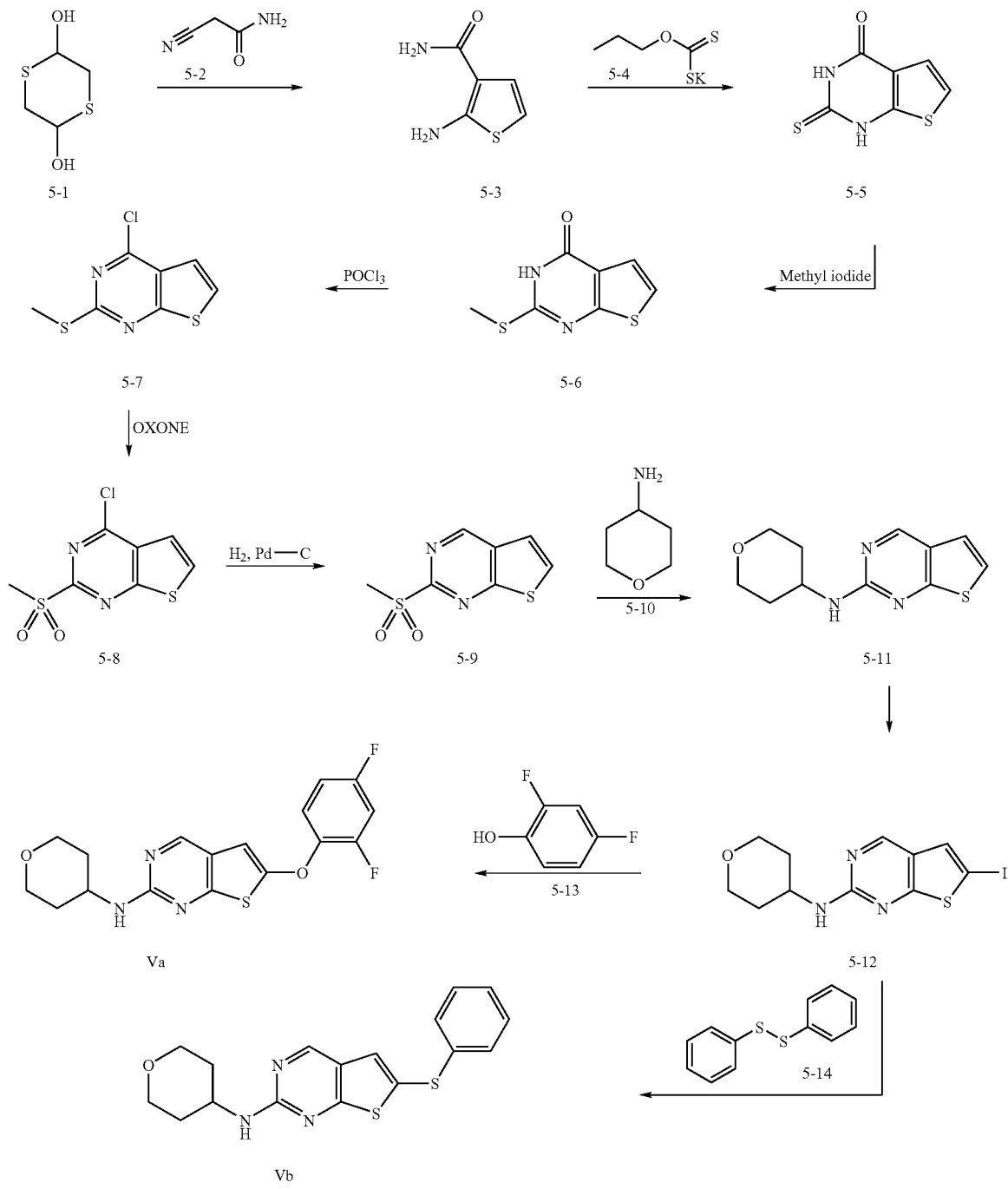

medicaments, e.g. in the form of pharmaceutical preparations. The pharmaceutical preparations can be administered enterally, e.g. orally in the form of tablets, coated tablets, dragees, hard and soft gelatine capsules, solutions, emulsions or suspensions, nasally, e.g. in the form of nasal sprays, or rectally, e.g. in the form of suppositories. However, they may also be administered parenterally, e.g. in the form of injection solutions.

The compounds of formula I and their aforementioned pharmaceutically acceptable salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain therapeutically valuable substances other than the compounds of formula I and their aforementioned pharmaceutically acceptable salts.

Medicaments which contain a compound of formula I or a pharmaceutically acceptable salt of a basic compound of formula I with an acid in association with a compatible pharmaceutical carrier material are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and their aforementioned pharmaceutically acceptable salts can be used in accordance with the invention as therapeutically active substances, especially as antiinflammatory agents or for the prevention of graft rejection following transplant surgery. The dosage can vary within wide limits and will, of course, be fitted to the individual requirements in each particular case. In general, in the case of administration to adults a convenient daily dosage should be about 0.1 mg/kg to about 100 mg/kg, preferably about 0.5 mg/kg to about 5 mg/kg. The daily dosage may be administered as a single dose or in divided doses and, in addition, the upper dosage limit referred to earlier may be exceeded when this is found to be indicated.

Finally, the use of compounds of formula I and their aforementioned pharmaceutically acceptable salts for the production of medicaments, especially in the treatment or prophylaxis of inflammatory, immunological, oncological, bronchopulmonary, dermatological and cardiovascular disorders, in the treatment of asthma, central nervous system disorders or diabetic complications or for the prevention of graft rejection following transplant surgery, is also an object of the invention.

Methods of Using the Compounds and Compositions

Compounds of Formula I are useful for, but not limited to, the treatment of any disorder or disease state in a human, or other mammal, which is exacerbated or caused by excessive or unregulated TNF or p38 kinase production by such mammal. Compounds of Formual I inhibit p38 kinase in in vitro assays and inhibit TNF-α release in cell based assays inhibiting as described in Examples 12 and 13. Accordingly, the present invention provides a method of treating a cytokine-mediated disease which comprises administering an effective cytokine-interfering amount of a compound of Formula I, or a pharmaceutically acceptable salt or a tautomer thereof.

Compounds of Formula I are useful for, but not limited to, the treatment of inflammation in a subject, and for use as antipyretics for the treatment of fever. Compounds of the invention are also useful in treating arthritis, including but not limited to, rheumatoid arthritis, spondyloarthropathies, gouty arthritis, osteoarthritis, systemic lupus erythematosus and juvenile arthritis, and other arthritic conditions. In addition, compounds of the present invention are useful in treating pulmonary disorders or lung inflammation, including adult respiratory distress syndrome, pulmonary sarcoidosis, asthma, silicosis, and chronic pulmonary inflammatory disease. Furthermore, compounds of the present invention are also useful in treating viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. Moreover, compounds of the present invention are also useful in the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds of the present invention are also useful for the treatment of influenza, multiple sclerosis, cancer, diabetes, systemic lupus erthrematosis (SLE), skin-related conditions such as psoriasis, eczema, bums, dermatitis, keloid formation, and scar tissue formation. Compounds of the present invention are also useful in treating gastrointestinal conditions such as inflammatory bowel disease, Crohn's disease, gastritis, irritable bowel syndrome and ulcerative colitis. The compounds of the present invention can also be used in treating ophthalmic diseases, such as retinitis, retinopathies, uveitis, ocular photophobia, and of acute injury to the eye tissue. Compounds of the invention also would be useful for treatment of angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. In addition, compounds of the present invention are also useful for preventing the production of cyclooxygenase-2.

Besides being useful for human treatment, compounds of the present invention are also useful for veterinary treatment of companion animals, exotic animals and farm animals, including mammals, rodents, and the like. More preferred animals include horses, dogs, and cats.

Furthermore, compounds of the present invention can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-β (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following examples and the methods of preparation of the compounds are given to enable those skilled in the art to more clearly understand and practice the present invention. These examples are merely illustrative and are not intended to be limiting.

Example 1

2-(tetrahydropyran-4-ylamino)-6-(2-chlorobenzoyl) thieno[2,3-d]pyrimidine

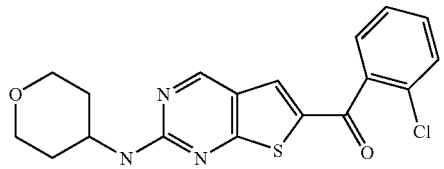

This example illustrates the preparation of a compound of formula I by the method described under scheme 1.

Step 1

4-fluoro-2-methylthiopyrimidine

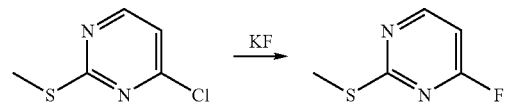

To a solution of 35.7 g (0.22 mol) of 4-chloro-2-methylthiopyrimidine (Aldrich Chemical Co., Milwaukee, Wis., USA) in 135 mL of tetraglyme was added 18-crown-6 (1.33 g) and potassium fluoride (Anhydrous, Aldrich Chemical Co., Milwaukee, Wis., USA, 80 g). The mixture was heated at 150° C.with stirring for 16 hours. The mixture was then cooled and distilled under reduced pressure to give 20 g (62%) of 4-fluoro-2-methylthiopyrimidine as a liquid.

Step 2

4-fluoro-2-methylthiopyrimidine-5-carboxaldehyde

To THF (100 mL) at −78° C. was added 2.5 M n-butyl lithium (20.4 mL). The mixture was warmed to 0° C. and diisopropyl amine (8.2 mL) was added slowly. The mixture was stirred at 0° C. for 30 minutes and then cooled to −78° C. A solution of 4-fluoro-2-methylthiopyrimidine (3.76 g, 22.2 mmol) in 5 mL of THF was slowly added and the mixture was stirred for 2 hours. Ethyl formate (4.3 mL, 44.4 mmol) was added and stirred for additional 2 hours. 4 N HCl (25 mL), ethanol (25 mL), and THF (100 mL) were slowly added and stirred for additional 10 min after the cooling bath was removed. The mixture was diluted with ethyl acetate (250 mL), water (200 mL), and saturated sodium bicarbonate (100 mL). The organic layer was separated and washed with brine (2×50 mL), dried over $MgSO_4$, and filtered. The solvent was removed to give a viscous oil (5.66 g).

Step 3

2-(methylthio)-6-(aroyl)thieno[2,3-d]pyrimidine

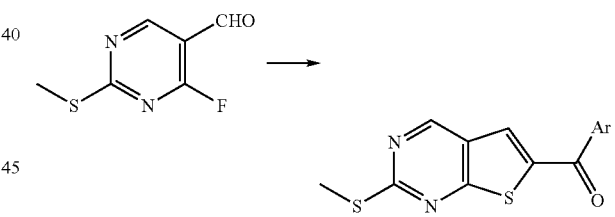

To a 0° C. solution of the crude 4-fluoro-2-methylthiopyrimidine-5-carboxaldehyde obtained in step 2 (2.8 g, approximately 11 mmol) and triethyl amine (1.44 mL) in THF (40 mL) was slowly added a solution of 2'-chloro-2-thioacetophenone (1.93 g) in THF (30 mL), (prepared as described in Step 3A below). The mixture was then slowly warmed to room temperature and stirred overnight. The resulting solution was added to a mixture of ethylacetate (500 mL) and water (250 mL). The organic layer was separated, washed with brine and sodium bicarbonate solution, dried, and evaporated. The crude product was purified by column chromatography (silica gel, 5–10% EtOAc/hexane) to give the desired product (1.82 g), MP 137–140.4° C.; MS: 321 (M+H).

Step 3A

2'-chloro-2-thioacetophenone

A mixture of 2'-chloroacetophenone (25 g, 0.162 mol) and copper bromide (72.8 g) in ethyl acetate (90 mL) and chloroform (90 mL) was refluxed for 2 hours. The mixture was cooled to room temperature, filtered through a pad of celite and washed with ethyl acetate. The solvents were removed to give crude 2-bromo-2'-chloroacetophenone (35 g).

A mixture of the above bromide (14.67 g) and potassium thioacetate (7.5 g) in acetone (250 mL) was stirred at room temperature overnight. An additional 3.7 g of possium thioacetate was added and the mixture was stirred for another day. The reaction mixture was filtered and washed with acetone. The filtrate was evaporated, and the residue was diluted with ethyl acetate (200 mL) and brine (150 mL). The organic layer was separated, dried, and evaporated to give crude 2-(acetylthiol)-2'-chloroacetophenone (14.4 g).

To a solution of the above product (2.29 g, 10 mmol) in methanol (100 mL) was slowly added a solution of sodium thiomethoxide (0.7 g, 10 mmol) in methanol (10 mL). The reaction mixture was stirred for 2 hours and poured into 200 mL of 0.1 M HCl and extracted with dichloromethane (2×150 mL). The organic phase was washed with brine (150 mL), dried, and evaporated to give the crude 2'-chloro-2-thioacetophenone (1.93 g).

Step 4

2-(methanesulfonyl)-6-(aroyl)thieno[2,3- d]Pyrimidine

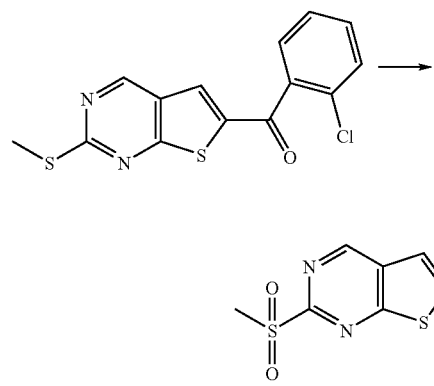

To a solution of the sulfide (1.6 g) obtained in Step 3 in THF (80 mL) was added a solution of Oxone (Aldrich, 6.13 g) in water (40 mL) at 0° C. The mixture was then stirred at room temperature for 5 hours. Ethyl acetate (250 mL) and water (150 mL) were added. The organic phase was separated, washed with water (2×150 mL), dried, and evaporated to give the sulfone (1.56 g), MP: 164.1–165.4° C. MS: 352.9 (M+H).

Step 5

2-(tetrahydropyran-4-ylamino)-6-(2-chlorobenzoyl)thieno [2,3-d]pyrimidine

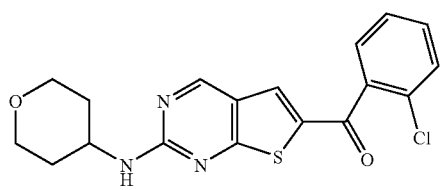

A mixture of the sulfone obtained above (352 mg) and 4-aminotetrahydropyran (152 mg) in NMP (0.1 mL) was heated at 100° C. for 3 hours. Ethyl acetate (180 mL) and water (50 mL) were added. The organic layer was separated, washed with brine, dried, and evaporated. The crude product was purified by preparative TLC (silica gel, 65% EtOAc/hexanes) to give 253 mg of the final product. It was converted to the hydrochloride salt by treatment with 1.5 equivalents of 1N HCl in ether. MS: 374 (M+H).

Example 2

2-(tetrahydropyran-4-ylamino)-6-(2-fluorobenzoyl) thieno[2,3-d]pyrimidine

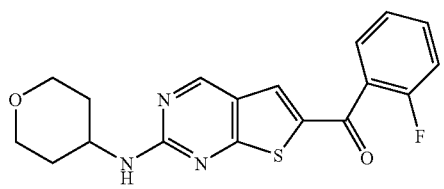

The above compound was prepared in a similar manner as described in example 1.

Example 2A 2-(tetrahydropyran-4-ylamino)-6-[(2-fluorophenyl) hydroxylmethyl]thieno[2,3-d]pyrimidine

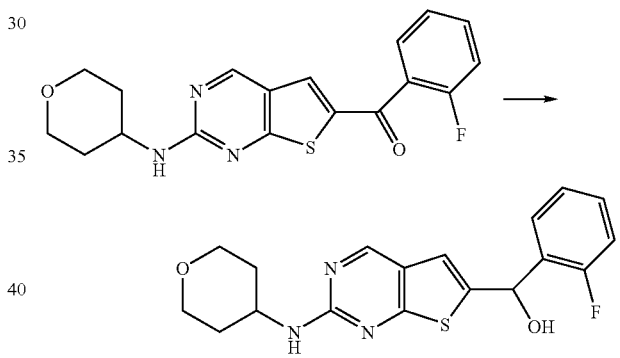

To a solution of 2-(tetrahydropyran-4-ylamino)-6-(2-fluorobenzoyl)thieno[2,3-d]pyrimidine (300 mg) in ethanol (30 mL) was added sodium borohydride (0.4 g) at room temperature and stirred overnight. Ethyl acetate (50 mL) was added to the reaction mixture. The organic layer was separated, washed with brine, dried, and evaporated. Purification by preparative TLC (silica gel, 50% EtOAc/hexanes) gave 140 mg of the alcohol. MS: 360.2 (M+H).

Example 2B 2-(tetrahydropyran-4-ylamino)-6-[(2-fluorophenyl) methyl]thieno[2,3-d]pyrimidine

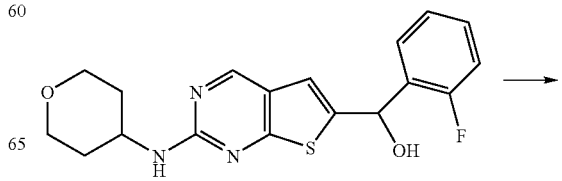

-continued

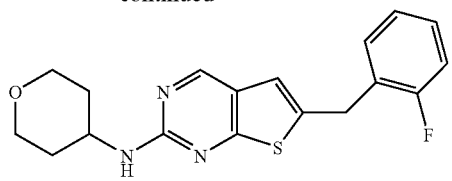

The alcohol (140 mg) obtained in Example 2A was stirred with triethylsilane (1.0 mL) and trifluoroacetic acid (1.5 mL) in dichloromethane (5 mL) for 4 hours. The solvents were removed. The residue was diluted with toluene (5 mL) and then concentrated. This dilution-concentration process was repeated three times. Purification with preparative TLC (50% EtOAc/Hexanes) gave the final product. It was converted to the hydrochloride salt with 1N HCl in ether to yield 65 mg of the salt. MP: 217–219° C. MS: 344 (M+H).

Example 3

2-(tetrahydropyran-4-ylamino)-6-(2-methoxybenzoyl)-7-methyl-pyrrolo[2,3-d]pyrimidine

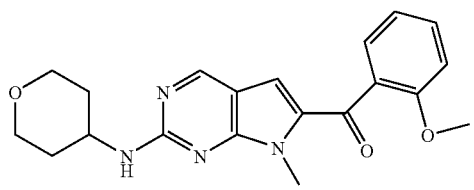

This example illustrates the method of making a compound of formula I according to the method described in Scheme 2.

Step 1

Ethyl 4-methylamino-2-methylthiopyrimidine-5-carboxylate

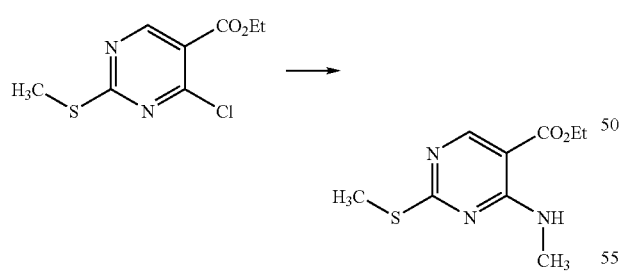

To a 0° C. solution of 20 g (86 mmol) of ethyl 4-chloro-2-methylthiopyrimidine-5-carboxylate (Aldrich Chemical Co., Milwaukee, Wis., USA) in 250 mL of dichloromethane was slowly added 35 mL (281 mmol) of a 33% solution of methylamine in ethanol. After stirring for 30 minutes, 150 mL of water was added and the phases were separated. The organic phase was dried over magnesium sulfate and filtered. The filtrate was evaporated under reduced pressure to give 19 g (97%) of ethyl 4-methylamino-2-methylthiopyrimidine-5-carboxylate as a white solid.

Step 2

4-methylamino-2-methylthiopyrimidine-5-methanol

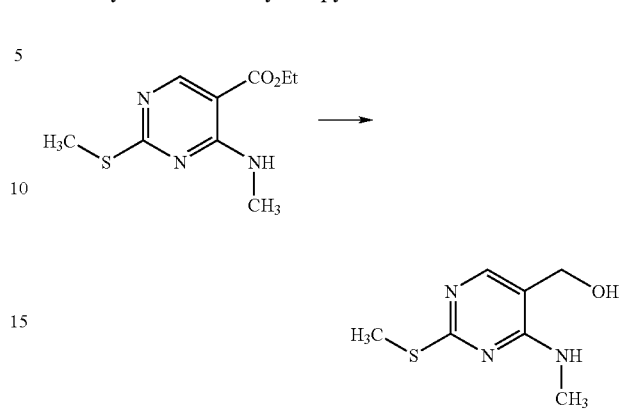

To a suspension of lithium aluminum hydride (9 g, 237 mmol) in 300 mL of dry tetrahydrofuran was added dropwise a solution of 34 g (143 mmol) of ethyl 4-methylamino-2-methylthiopyrimidine-5-carboxylate in 300 mL of dry tetrahydrofuran and left to stand for 15 minutes. The mixture was cooled in an ice bath and 18 mL of water was added dropwise followed by 36 mL of 2 M sodium hydroxide solution and 48 mL of additional water. The resulting suspension was stirred for 17 hours at room temperature and then filtered. The filter residue was washed twice with 100 mL of ethyl acetate, and the combined filtrate and washings were evaporated under reduced pressure. The residue was suspended in 200 mL of dichloromethane/hexane (2:1) and the solid was filtered and dried to give 23.5 g (86%) of 4-methylamino-2-methylthiopyrimidine-5-methanol as a yellow solid.

Step 3

4-methylamino-2-methylthiopyrimidine-5-carboxaldehyde

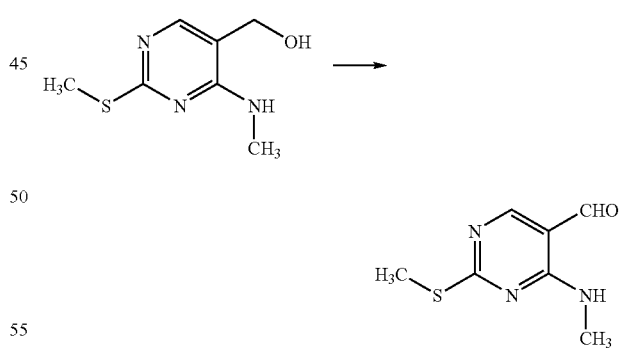

To a solution of 4-methylamino-2-methylthiopyrimidine-5-methanol (20 g, 108 mmol) in 1 L of dichloromethane was added 87 g (1 mol) of manganese dioxide. The resulting suspension was stirred for 24 hours and then filtered through a filter aid. The filter residue was washed with 100 mL of dichloromethane and the combined filtrate and washings were evaporated under reduced pressure to give 15.8 g (80%) of 4-methylamino-2-methylthiopyrimidine-5-carboxaldehyde as a white solid.

Step 4

2-(methylthio)-6-(2-methoxybenzoyl)-7-methyl-pyrrolo[2,3-d]pyrimidine

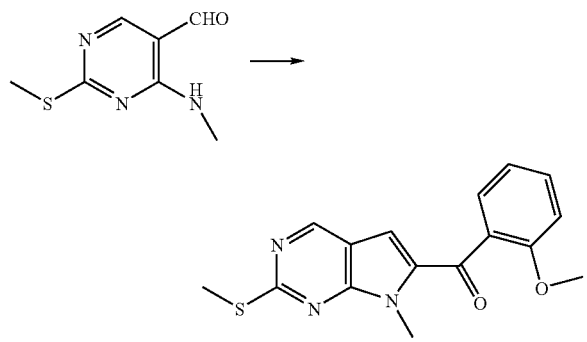

A mixture of the aldehyde (0.792 g), 2'-methoxy bromoacetophenone (1.17 g, Aldrich) and potassium carbonate (1.6 g) in NMP (5mL) was stirred at 70–80° C. overnight. Additional 2'-methoxy bromoacetophenone (0.88 g) was added and the mixture was stirred at 100° C. overnight. Additional 2'-methoxy bromoacetophenone (0.65 g) and potassium carbonate (1.12 g) were added and the mixture was again stirred at 100° C. overnight. The reaction mixture was cooled and diluted with ethyl acetate (150 mL) and washed with brine (3×50 mL), dried, and concentrated. Column chromatography (silica gel, 10–30% EtOAc/hexanes) followed by preparative TLC (silica gel, 30% EtOAc/hexanes) gave 100 mg of the product. MS: 334 (M+H).

Step 5

2-(tetrahydropyran-4-ylamino)-6-(2-methoxybenzoyl)-7-methyl-pyrrolo[2,3-d]pyrimidine

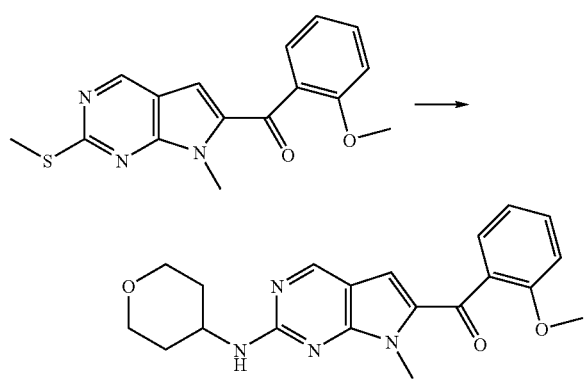

The sulfide (0.1 g) obtained in the Step 4 above was stirred with oxone (0.5 g) in THF/H$_2$O (2 mL/2 mL) for 4 hours. Aqueous workup with ethyl acetate and brine gave the crude sulfone.

The sulfone obtained above was heated with 4-aminotetrahydropyran (0.18 g) in NMP (0.2 mL) at 140° C. overnight. An aqueous work up gave the crude product. Purification by preparative TLC gave the desired product (2 mg). MS: 367 (M+H).

Example 4

2-(cyclopentylamino)-6-benzyl-furano[2,3-d]pyrimidine

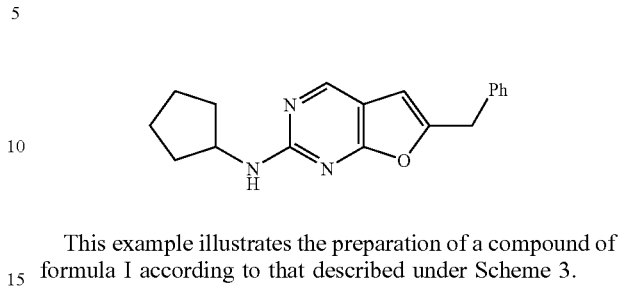

This example illustrates the preparation of a compound of formula I according to that described under Scheme 3.

Step 1

2-(methylthio)-6-benzyl-furano[2,3-d]pyrimidine

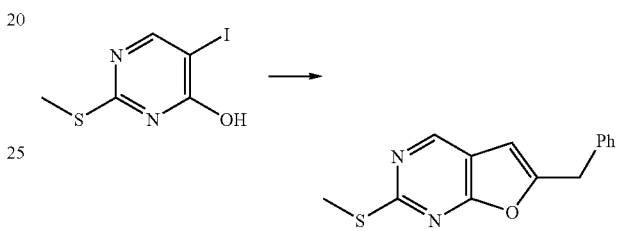

A mixture of 2-methylthio-4-hydroxy-5-iodopyrimidine (2.65 g), 3-phenyl-1-propyne (1.49 mL), copper (I) iodide (90 mg) and bis(triphenylphosphine) Palladium (II) dichloride (Fluka, 160 mg) in 20 mL of triethylamine and NMP (7 mL) was stirred at 40° C. for 6 hours. The reaction mixture was diluted with ethyl acetate (100 mL), washed with brine (3×50 mL), concentrated and purified by column chromatography (5% EtOAc/hexanes) to give 0.57 g of a solid product. MP: 69–72.2° C. MS: 257.2 (M+H).

Step 2

2-(cyclopentylamino)-6-benzyl-furano[2,3-d]pyrimidine

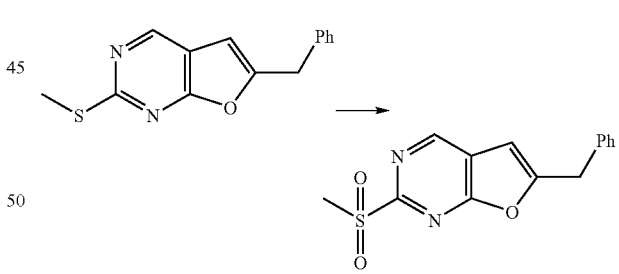

A solution of the sulfide (0.57 g) obtained in Step 1 above in THF (15 mL) was stirred with oxone (2.2 g) in water (15 mL) at 0° C. for 3 hours and at room temperature for 1 hour. An aqueous work up gave the crude sulfone (containing sulfoxide) (0.63 g).

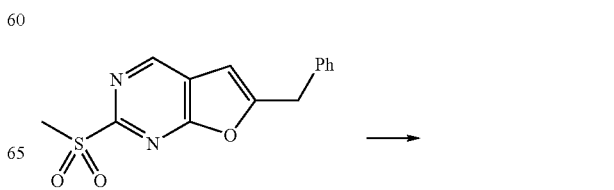

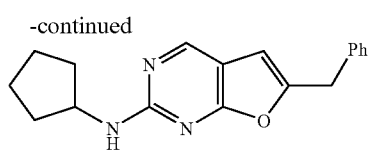

A solution of the sulfone (60 mg) thus obtained in 1 mL of aminocyclopentane was stirred at 100° C. for 2 hours. The excess aminocyclopentane was removed. The crude product was purified by preparative TLC (40% EtOAc/hexanes) to give 47 mg of a solid product. MS: 294.2 (M+H).

Example 5

2-(cyclopentylamino)-6-benzyl-7-methyl-pyrrolo[2,3-d]pyrimidine

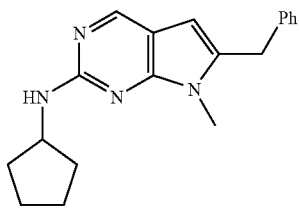

This example illustrates the preparation of 2-(cyclopentylamino)-6-benzyl-7-methyl-pyrrolo[2,3-d]pyrimidine according to that described in Scheme 4.

Step 1

2-methylthio-5-(3-phenylpropyn-1-yl)-6-methylaminopyrimidine

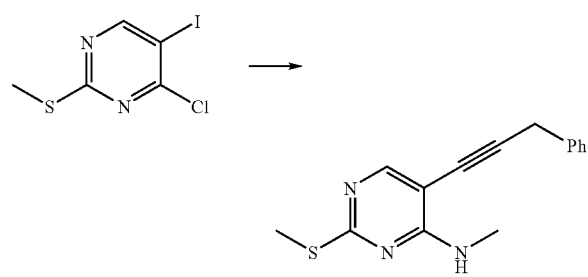

A mixture of 2-methanethio-4-chloro-5-iodopyrimidine (6.5 g), 3-phenyl-1-propyne (3.4 mL), copper (I) iodide (130 mg), bis(triphenylphosphine)palladium(II) dichloride (322 mg), and triethylamine (25 mL) was heated in NMP at 40° C. for 2 hours. The mixture was cooled to 0° C. and 25 mL of 40% methylamine (Aldrich) in acetonitrile (15 mL) was added. The resulting mixture was stirred at room temperature for 2 hours and then concentrated. The residue was diluted with ethyl acetate (200 mL) and washed with brine (3×100 mL). The organic layer was separated, dried and evaporated to give an oil. Column chromatography purification (5–12% EtOAc/hexanes) gave 3.8 g of a solid product. MS: 270 (M+H).

Step 2

2-(methylthio)-6-benzyl-7-methyl-pyrrolo[2,3-d]pyrimidine

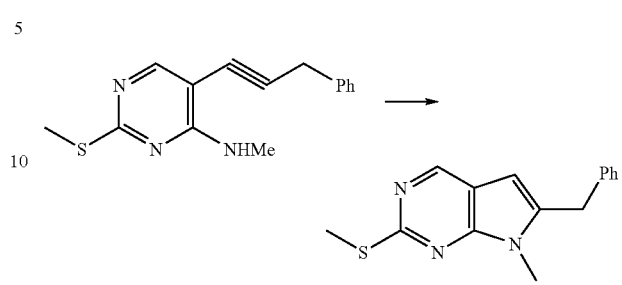

A mixture of the alkyne obtained above (3.47 g), triethylamine (15 mL), copper (I) iodide (200 mg), bis(triphenylphosphine)palladium dichloride (200 mg) in NMP (10 mL) was refluxed for 6 hours. Aqueous work up gave 4 g of dark residue. Column chromatography purification (10–13% EtOAc/hexanes) gave 1.0 g of the product. MS: 270.2 (M+H).

Step 3

2-(methanesulfinyl)-6-benzyl-7-methyl-pyrrolo[2,3-d]pyrimidine

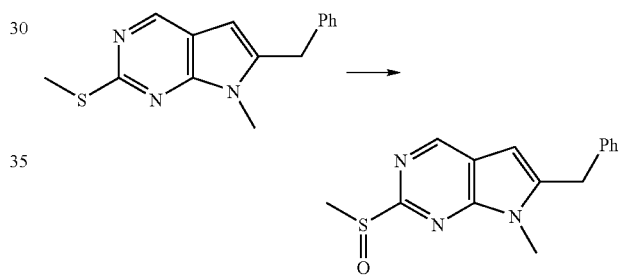

The sulfide (0.3 g) in THF (10 mL) was stirred with a solution of oxone (0.9 g) in water (10 mL) at 0–5° C. for 3 hours. Aqueous work up gave the sulfoxide (containing sulfone).

Step 4

2-(cyclopentylamino)-6-benzyl-7-methyl-pyrrolo[2,3-d]pyrimidine

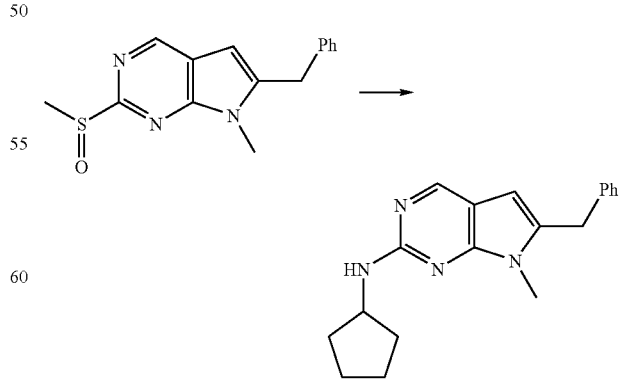

A mixture of the sulfoxide (50 mg) from Step 3 and cyclopentylamine (1 mL) was stirred at 100° C. overnight.

Excess cyclopentylamine was removed and the residue was purified by preparative TLC (25% EtOAc/hexanes) to give the desired product (26 mg). MS: 307.3 (M+H).

Example 6

(Tetrahydropyran-4-yl)-thieno[23-d]pyrimidin-2-yl-amine

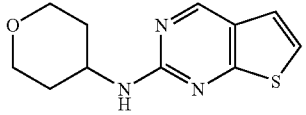

Step 1

2-Amino-thiophene-3-carboxlic acid amide

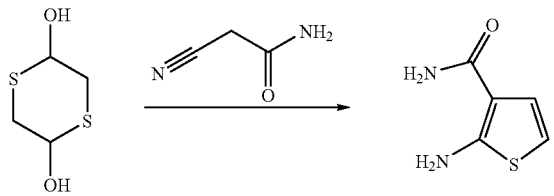

2,5-Dihydroxy-1,4-dithiane (76 g) and cyanoacetamide (84 g) were added to a mixture of methanol (180 mL), water (10 mL) and triethylamine (10 g). The resulting mixture was heated at 35–40° C. for about 30 minutes while stirring, and then heated to 50–60° C. for an additional 30 minutes with stirring. The reaction mixture was then cooled to room temperature and poured into a mixture of ice (100 g)/water (300 mL). A fine precipitate formed upon addition, which was filtered and dried overnight to give 100.6 g of the title compound as a pale gray powder ((M+H)$^+$=143, M.P.=159.0–159.6° C.).

Step 2

2-Thioxo-2,3-dihydro-1H-thieno[2,3-d]pyrimidin-4-one

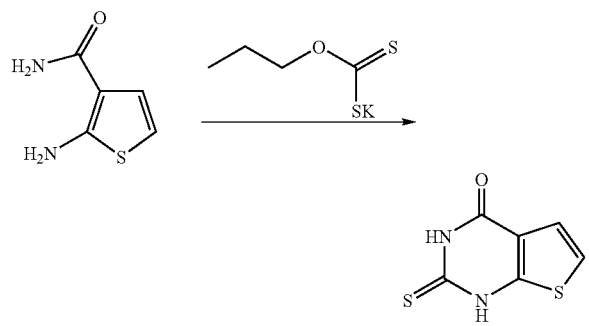

2-Amino-thiophene-3-carboxlic acid amide (28.4 g, 0.2 mol) and potassium ethylxanthate (96 g, 3 eq) were mixed together and added to DMF (1000 mL). The resulting mixture was heated to 150° C. for about six hours. The solvent (DMF) was removed on the rotovap under high vacuum at 90° C. The residue was diluted with 600 mL of aqueous citric acid (5%) and cooled to 0° C. and stirred for about 30 minutes. The tan powder was filtered and dried overnight to give 25.6 g of the title compound ((M+H)$^+$=185, M.P.>300° C.).

Step 3

2-Methylsulfanyl-3H-thieno[2,3-d]pyrimidin-4-one

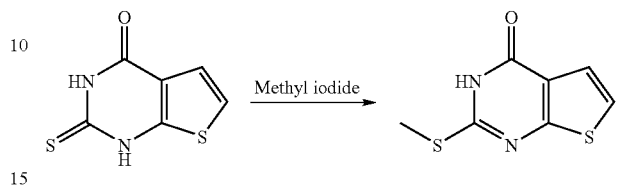

To a solution of 2-thioxo-2,3-dihydro-1H-thieno[2,3-d]pyrimidin-4-one (25.4 g, 0.138 mol) in 1N aqueous NaOH (600 mL) at room temperature was added methyl iodide (10.3 mL, 1.2 eq). The resulting mixture was stirred vigorously for about 2.5 hours. The reaction mixture was cooled to 0° C. and acetic acid was added (about 80 mL) until about pH=4.5 was reached. A fine precipitate was filtered and dried overnight to afford the title compound as a fine tan powder (24.8 g) (M$^+$=198, M.P.=231.6–235.0° C.).

Step 4

4—Chloro-2-methylsulfanyl-thieno[2,3-d]pyrimidine

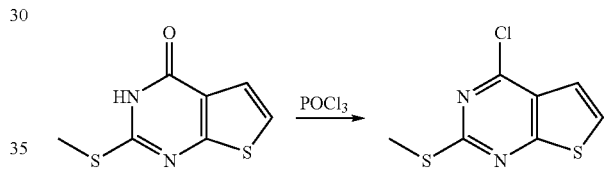

2-Methylsulfanyl-3H-thieno[2,3-d]pyrimidin-4-one (12 g, 60.5 mmol) was combined with POCl$_3$ (56 mL), and the resulting mixture was heated to reflux for about 1 hour. The reaction mixture was concentrated under reduced pressure at 50° C. The residue was diluted with ethyl acetate (700 mL) at 0° C. Saturated sodium bicarbonate solution (600 mL) was added slowly. The resulting mixture was stirred vigorously at 0° C. for one hour and the layers were separated. Saturated sodium bicarbonate solution (600 mL) was added to the organic layer at 0° C., and the mixture was stirred vigorously for 20 minutes. The layers were separated. Brine (600 mL) was added to the organic layer and stirred vigorously for 5 minutes, and the layers were again separated. The organic layer was dried over magnesium sulfate, filtered and concentrated to afford the title compound (10.7 g) as a dark tan powder (M$^+$=216, M.P.=105.0–107.4° C.).

Step 5

4—Chloro-2-methanesulfonyl-thieno[2,3-d]pyrimidine

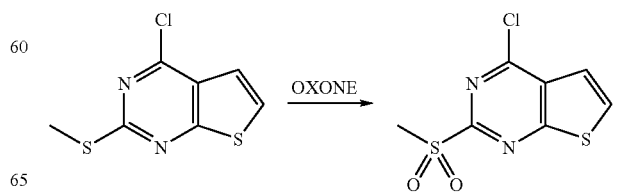

To a solution of 4-chloro-2-methylsulfanyl-thieno[2,3-d]pyrimidine (10 g, 46.15 mmol) in tetrahydrofuran (350 mL) at 0° C. was added a solution of OXONE (59.6 g, 2.1 eq) in water (300 mL) dropwise with stirring. The resulting mixture was gradually warmed from 0° C. to room temperature overnight. The reaction mixture was diluted with ethyl acetate (1000 mL) and water (300 mL), and the layers were separated. The aqueous layer was extracted with ethyl acetate (1×300 mL). Organic layers were combined, washed with brine (2×300 mL), dried over magnesium sulfate, filtered and concentrated to give 10.7 g of the title compound as a tan powder (M+H)$^+$=249.

Step 6

2-Methanesulfonyl-thieno[2,3-d]pyrimidine

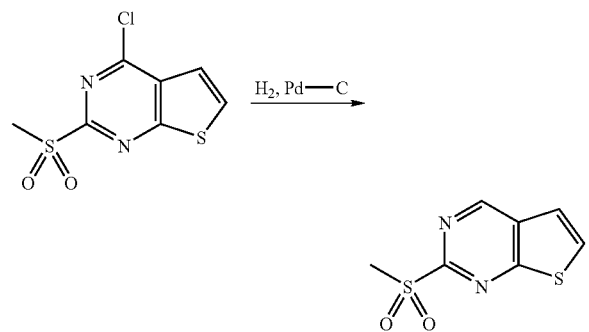

Nitrogen gas was bubbled through a solution of 4-chloro-2-methanesulfonyl-thieno[2,3-d]pyrimidine (2.8 g) in ethanol (400 mL) and tetrahydrofuran (75 mL) for 5 minutes. To this solution was added 10% palladium on activated charcoal (2.8 g). The resulting mixture was placed on a Parr shaker under 30 psi of hydrogen gas. After 16 hours, additional catalyst (1 g) was added, and the mixture was again placed on the Parr shaker under 30 psi hydrogen gas for additional 6 hours. The reaction mixture was filtered through a 3 cm bed of celite. The filter cake was washed with dichloromethane. Concentration of the filtrate gave the title compound (2.2 g).

Step 7

(Tetrahydropyran-4-yl)-thieno[2,3-d]pyrimidin-2-yl-amine

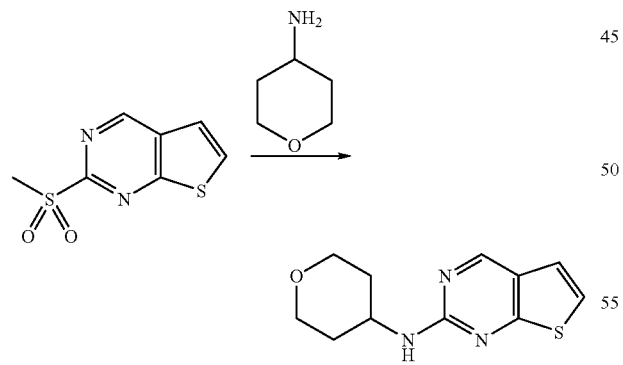

A mixture of 2-methanesulfonyl-thieno[2,3-d]pyrimidine (1.58 g, 7.37 mmol), 4-aminotetrahydropyran (2.24 g, 3 eq) and 1-methyl-2-pyrolidinone (2 mL) was heated to 100° C. with stirring for about 7 hours and continued heating at 80° C. overnight. The reaction mixture was cooled to room temperature and diluted with ethyl acetate (180 mL)/water (60 mL). The layers were separated, and the organic layer was washed successively with water (4×60 mL) and brine (1×60 mL). The organic layer was then dried over magnesium sulfate, filtered and concentrated to give 1.7 g of the crude product. Purification by column chromatography on silica gel eluting with 25% ethyl acetate in hexanes afforded the title compound as a white powder (1.264 g) ((M+H)$^+$=236, M.P.=127.0–130.0° C.).

Example 7

6-Iodo-thieno[2,3-d]pyrimidin-2-yl)-(tetrahydropyran-4-yl)-amine

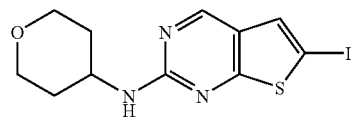

Step 1

6-Iodo-thieno[2,3-d]pyrimidin-2-yl)-(tetrahydropyran-4-yl)-amine

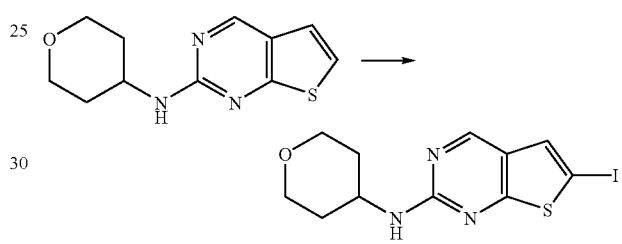

To a solution of (tetrahydro-pyran-4-yl)-thieno[2,3-d]pyrimidin-2-yl-amine (786 mg, 3.34 mmol) in benzene (40 mL) was added mercury(II) oxide (854 mg, 1.18 eq) followed by iodine (1.00 g, 1.18 eq). The resulting mixture was stirred vigorously at room temperature overnight. Additional mercury(II) oxide (427 mg, 0.6 eq) and iodine (500 mg, 0.6 eq) were added, and the mixture was again stirred vigorously at room temperature for one additional day. The reaction mixture was then filtered through a 3 cm bed of celite and washed with ethyl acetate (180 mL). The filtrate was washed successively with saturated aqueous solution of Na$_2$S$_2$O$_3$ (4×50 mL), water (2×50 mL) and brine (1×50 mL). The organic layer was dried over magnesium sulfate, filtered and concentrated to give the title compound as a reddish powder (823 mg) (M+H)$^+$=362.

Example 8

[6-(2,4-Difluorophenoxy)thieno[2,3-d]pyrimidin-2-yl]-(tetrahydropyran-4-yl)-amine

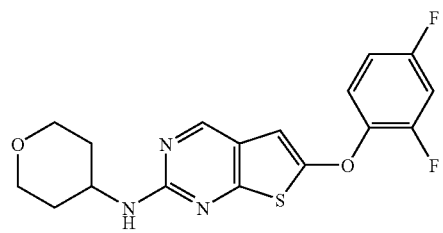

Step 1

[6-(2.4-Difluorophenoxy)thieno[2,3-d]pyrimidin-2-yl]-(tetrahydropyran-4-yl)-amine

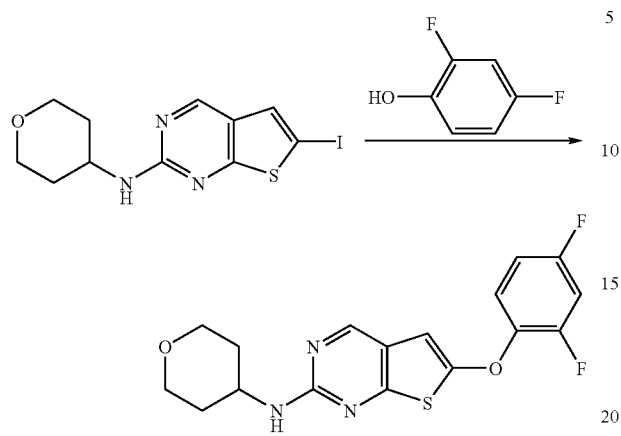

A mixture of 2,4-difluorophenol (0.5 mL, 38 eq), sodium hydride (205 mg, 37 eq) and 1-methyl-2-pyrolidinone (0.6 mL) in a 2.5 mL microwave reactor vessel was stirred for about 5 minutes. To this mixture was added 6-iodo-thieno[2,3-d]pyrimidin-2-yl)-(tetrahydropyran-4-yl)-amine (50 mg, 0.14 mmol), and the resulting mixture was placed on a microwave reactor for 75 minutes at 150° C. The reaction mixture was then cooled to room temperature, diluted with ethyl acetate (85 mL) and washed successively with water (3×30 mL) and brine (1×30 mL). The ethyl acetate layer was concentrated and then purified by Preparative Thin Layer Chromatography eluting on two (20×20 cm, 1000 μM) silica gel plates with 40% ethyl acetate in hexanes. The title compound was isolated as an off-white powder (8 mg) $(M+H)^+=364$.

Example 9

[6-(2,4-Difluorophenylsulfanyl)thieno[2,3-d]pyrimidin-2-yl]-(tetrahydropyran-4-yl)-amine

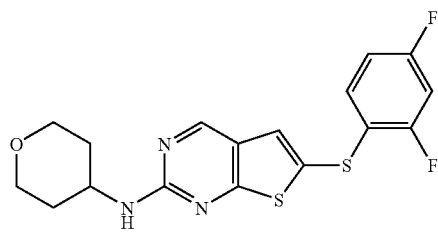

Step 1

[6-(2,4-Difluorophenylsulfanyl)thieno[2,3-d]pyrimidin-2-yl]-(tetrahydropyran-4-yl)-amine

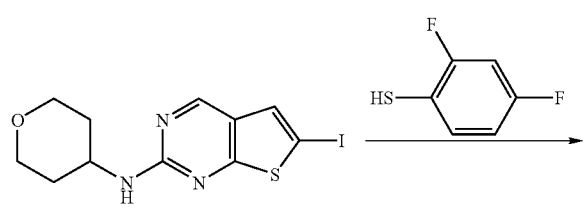

-continued

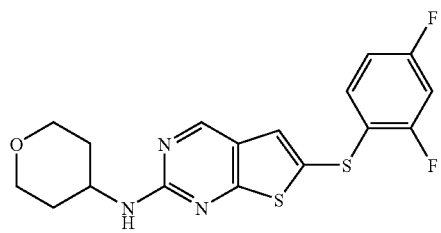

2,4-Difluorobenzenethiol (0.35 mL, 10.8 eq) was added to 6-iodo-thieno[2,3-d]pyrimidin-2-yl)-(tetrahydropyran-4-yl)-amine (100 mg, 0.277 mmol), and the resulting mixture was stirred overnight at room temperature. The reaction mixture was then heated 100° C. with stirring for 5 hours, after which 1-methyl-2-pyrolidinone (0.2 mL) was added followed by potassium carbonate (415 mg, 10.8 eq). The resulting mixture was heated with stirring to 150° C. for an additional 5 hours. The reaction mixture was then cooled to room temperature and diluted with ethyl acetate (35 mL)/water (20 mL). The layers were separated. The organic layer was washed with successively with water (3×20 mL) and brine (1×20 mL), dried over magnesium sulfate, filtered and concentrated to yield a crude product (452 mg), which was purified by Preparative Thin Layer Chromatography eluting on four (20×40 cm, 1000 μM) silica gel plates with 55% ethyl acetate in hexanes to afford the title compound (16 mg) as an off-white powder $(M+H)^+=380$.

Example 10

(6-Phenylsulfanylthieno[2,3-d]pyrimidin-2-yl)-(tetrahydropyran-4-yl)-amine

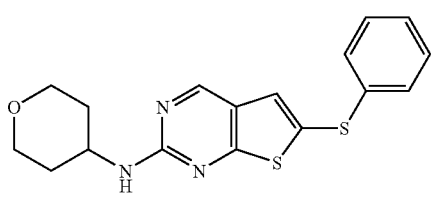

Step 1

(6-Phenylsulfanylthieno[2,3-d]pyrimidin-2-yl)-(tetrahydropyran-4-yl)-amine

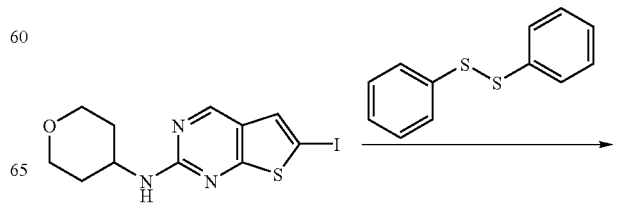

-continued

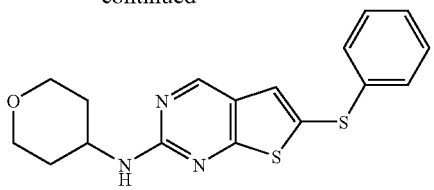

To a solution of 6-iodothieno[2,3-d]pyrimidin-2-yl)-(tetrahydropyran-4-yl)-amine (100 mg, 0.277 mmol) in tetrahydrofuran (3 mL) at −78° C. was added 2.5M n-butyllithium in hexanes (0.23 mL, 2.1 eq) dropwise. The reaction mixture turned from red to yellow. The resulting mixture was stirred at −78° C. for 45 minutes before slowly adding a solution of phenyl disulfide (242 mg, 4 eq) in tetrahydrofuran (3 mL) at −78° C. The reaction was gradually warmed from −78° C. to room temperature over 4 hours and quenched by adding water (5 mL). The resulting mixture was diluted with ethyl acetate (35 mL)/water (25 mL). The layers were partitioned, and the separated organic layer was washed with brine (1×20 mL), dried over magnesium sulfate, filtered and concentrated to give the crude product. Purification by Preparative Thin Layer Chromatography eluting on two (20×20 cm, 1000 μM) silica gel plates with 50% ethyl acetate in hexanes afforded the title compound (16 mg) as an off-white powder (M+H)$^+$=344.

Example 11

The following are representative pharmaceutical formulations containing a compound of Formula (I).

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| Sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

Injectable Formulation

The following ingredients are mixed to form an injectable formulation.

| Ingredient | Amount |
| --- | --- |
| compound of this invention | 0.2 g |
| sodium acetate buffer solution, 0.4 M | 2.0 ml |
| HCl (1N) or NaOH (1N) | q.s. to suitable pH |
| water (distilled, sterile) | q.s. to 20 ml |

All of the above ingredients, except water, are combined and heated to 60–70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., N.Y.), and has the following composition:

| | |
| --- | --- |
| compound of the invention | 500 mg |
| Witepsol ® H-15 | balance |

Example 12

Inhibition Of p-38 (MAP) Kinase-In Vitro Assay

The p-38 MAP kinase inhibitory activity of compounds of this invention in vitro was determined by measuring the transfer of the γ-phosphate from γ-$^{33}$P-ATP by p-38 kinase to Myelin Basic Protein (MBP), using the a minor modification of the method described in Ahn, N. G.; et al. *J. of Biol. Chem*. Vol. 266(7), 4220–4227, (1991)

The phosphorylated form of the recombinant p38 MAP kinase was expressed with SEK-1 and MEKK in *E. Coli* (see, Khokhlatchev, A. et al. *J. of Biol. Chem*. Vol. 272(17), 11057–11062, (1997) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis(beta-aminoethyl ether)-N,N,N',N'-tetraacetic acid, 1 mM sodium vanadate, 1 mM dithiothreitol, 40 mM magnesium chloride). Test compound dissolved in DMSO or only DMSO (control) was added and the samples were incubated for 10 min. at 30° C. The kinase reaction was initiated by the addition of a substrate cocktail containing MBP and γ-$^{33}$P-ATP. After incubating for an additional 20 min. at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

The p-38 inhibitory activities (expressed as IC$_{50}$, the concentration causing 50% inhibition of the p-38 enzyme being analyzed) of the compounds listed in Table 1 in the specification are between 0.01 μM and 10 μM. Selected data are shown below.

| Compound | Structure | p38 IC$_{50}$ (nM) |
|---|---|---|
| 1 | 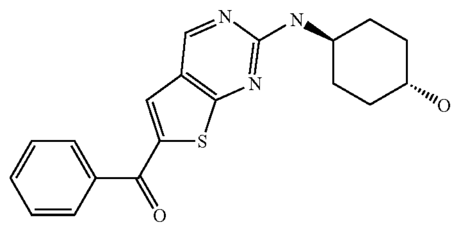 | 104 |
| 3 | 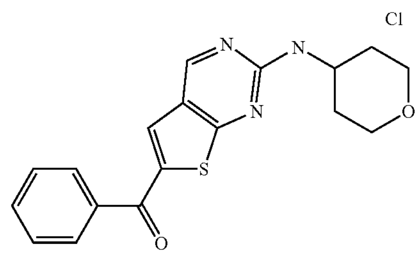 | 221 |
| 23 | 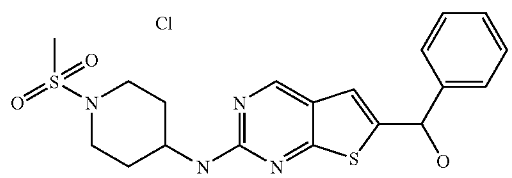 | 128 |
| 30 | 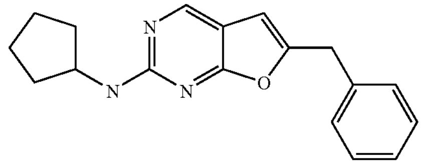 | 744 |
| 33 | 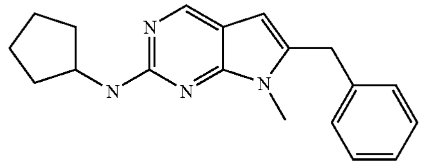 | 135 |
| 41 | 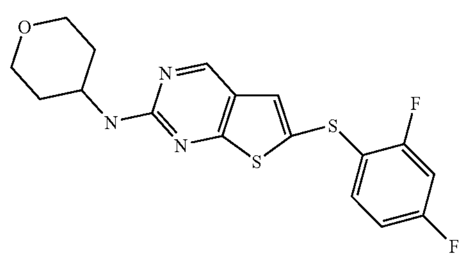 | 226 |

Example 13

This example illustrates an in vitro assay to evaluate the inhibition of LPS-induced TNF-α production in THP1 cells.

The ability of the compounds of this invention to inhibit the TNF-α release was determined using a minor modification of the methods described in Blifeld, et al. *Transplantation*, 51:498–503 (1991).

(a) Induction of TNF Biosynthesis:

THP-1 cells were suspended in culture medium [RPMI (Gibco-BRL, Gailthersburg, Md.) containing 15% fetal bovine serum, 0.02 mM 2-mercaptoethanol], at a concentration of $2.5 \times 10^6$ cells/mL and then plated in 96 well plate (0.2 mL aliquots in each well). Test compounds were dissolved in DMSO and then diluted with the culture medium such that the final DMSO concentration was 5%. Twenty five μL aliquots of test solution or only medium with DMSO (control) were added to each well. The cells were incubated for 30 min., at 37° C. LPS (Sigma, St. Louis, Mo.) was added to the wells at a final concentration of 0.5 μg/ml, and cells were incubated for an additional 2 h. At the end of the incubation period, culture supernatants were collected and the amount of TNF-α present was determined using an ELISA assay as described below.

(b) ELISA Assay:

The amount of human TNF-α present was determined by a specific trapping ELISA assay using two anti-TNF-α antibodies (2TNF-H12 and 2TNF-H34) described in Reimund, J. M., et al. *GUT*. Vol. 39(5), 684–689 (1996).

Polystyrene 96-well plates were coated with 50 μl per well of antibody 2TNF-H12 in PBS (10 μg/mL) and incubated in a humidified chamber at 4° C. overnight. The plates were washed with PBS and then blocked with 5% nonfat-dry milk in PBS for 1 hour at room temperature and washed with 0.1% BSA (bovine serum albumin) in PBS.

TNF standards were prepared from a stock solution of human recombinant TNF-α (R&D Systems, Minneapolis, Minn.). The concentration of the standards in the assay began at 10 ng/mL followed by 6 half log serial dilutions.

Twenty five μL aliquots of the above culture supernatants or TNF standards or only medium (control) were mixed with 25 μL aliquots of biotinylated monoclonal antibody 2TNF-H34 (2 μg/mL in PBS containing 0.1% BSA) and then added to each well. The samples were incubated for 2 hr at room temperature with gentle shaking and then washed 3 times with 0.1% BSA in PBS. 50 μl of peroxidase-streptavidin (Zymed, S. San Francisco, Calif.) solution containing 0.416 μg/mL of peroxidase-streptavidin and 0.1% BSA in PBS was added to each well. The samples were incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) was added to each well and the samples were incubated in the dark for 30 min., at room temperature. Optical density of the sample and the reference were read at 450 nm and 650 nm, respectively. TNF-α levels were determined from a graph relating the optical density at 450 nm to the concentration used.

The $IC_{50}$ value was defined as the concentration of the test compound corresponding to half-maximal reduction in 450 nm absorbance.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All publications, patents, and patent applications cited herein are hereby incorporated by reference in their entirety for all purposes.

What is claimed is:

1. A compound represented by Formula V:

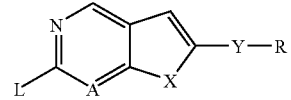

Formula V wherein:

A is N;

X is O, $NR^3$ or S, wherein $R^3$ is hydrogen, alkyl or aryl;

and Y is a bond, O, NR', C(=O), CH(OR'), CH(R'), or $S(O)_n$, wherein n is 0, 1, or 2;

and R' is hydrogen or alkyl;

R is aryl or heteroaryl;

and L is $R^a$—$S(O)_{n1}$, where $R^a$ is alkyl or aryl and n1 is 0, 1 or 2 wherein aryl is unsubstituted or substituted with 1, 2, or 3 substituents selected from the group alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl, —Y-heterocyclyl, —Y—$OR^p$, —Y—$NR^pR^q$, —Y—C(O)—$R^p$, —YS$(O)_{0-2}R^p$, —Y—N—$S(O)_{0-2}R^p$, —Y—$S(O)_2NR^pR^q$, —Y—N—C(O)$NR^pR^q$, where Y is a bond or $C_1$–$C_3$ alkylene, $R^p$ and $R^q$ are each independently selected from hydrogen, alkyl, haloalkyl, hydroxy, alkoxy, aryl, heteroaryl, cycloalkyl, and heterocyclyl, with the proviso that when the substituent is —YS$(O)_{1-2}R^p$ or —Y—N—S(O)$^2R^p$ said $R^p$ is not hydrogen; heteroalkyl is unsubstituted or substituted with 1 or 2 substituents selected from the group alkyl, haloalkyl, heteroalkyl, heterocyclyl, halo nitro, cyano, carboxy, acyl, —(alkylene)$_n$—COOR, and —(alkylene)$_n$—CONR$^a$R$^b$, where n is 0 or 1, R is hydrogen, alkyl, optionally substituted phenylalkyl, or optionally substituted heteroaralkyl, $R^a$ and $R^b$ are each independently hydrogen, alkyl, cycloalkyl, cycloalkylalkyl, hydroxyalkyl, aryl, or $R^a$ and $R^b$ together with the nitrogen atom to which they are attached form heterocyclyl or heteroaryl.

2. The compound of claim 1, wherein n1 is 2.

3. The compound of claim 2, wherein X is S.

4. A compound of Formula VI

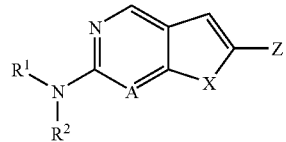

Formula VI wherein:
A is N;
R¹ is hydrogen, alkyl or arylalkyl;
R² is alkyl, heteroalkyl, (R")₂NCO-alkylene- (where each R" is independently hydrogen or alkyl), cycloalkyl, heterocyclyl, aryl, or heteroaryl;
X is S;
and Z is hydrogen or halo
wherein aryl is unsubstituted or substituted with 1, 2, or 3 substituents selected from the group alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl,—Y-heterocyclyl, —Y—OR$^p$, —Y—NR$^p$R$^q$, —Y—C(O)—R$^p$, —YS(O)$_{0-2}$R$^p$, —Y—N—S(O)$_{0-2}$R$^p$, —Y—S(O)₂NR$^p$R$^q$, —Y—N—C(O)NR$^p$R$^q$, where Y is a bond or C₁–C₃ alkylene, R$^p$ and R$^q$ are each independently selected from hydrogen, alkyl, haloalkyl, hydroxy, alkoxy, aryl, heteroaryl, cycloalkyl, and heterocyclyl, with the proviso that when the substituent is —YS(O)$_{1-2}$R$^p$ or —Y—N—S(O)²R$^p$ said R$^p$ is not hydrogen; heteroaryl is unsubstituted or substituted with 1 or 2 substituents selected from the group alkyl, haloalkyl, heteroalkyl, heterocyclyl, halo nitro, cyano, carboxy, acyl, —(alkylene)$_n$—COOR, and —(alkylene)$_n$—CONR$^a$R$^b$, where n is 0 or 1, R is hydrogen, alkyl, optionally substituted phenylalkyl, or optionally substituted heteroaralkyl, R$^a$ and R$^b$ are each independently hydrogen, alkyl, cycloalkyl, cycloalkylalkyl, hydroxyalkyl, aryl, or R$^a$ and R$^b$ together with the nitrogen atom to which they are attached form heterocyclyl or heteroaryl.

5. The compound of claim 4, wherein: R¹ is hydrogen; and R² is alkyl, hydroxyalkyl, cycloalkyl, heterocyclyl or aryl.

6. A process for producing a compound of the formula:

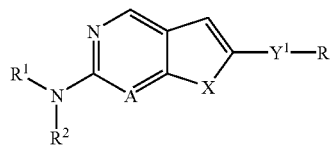

IA wherein A is N;
R is aryl or heteroaryl;
R¹ is hydrogen, alkyl or arylalkyl;
R² is alkyl, heteroalkyl, (R")₂NCO-alkylene- (where each R" is independently hydrogen or alkyl), cycloalkyl, heterocyclyl, aryl, or heteroaryl;
X is O, NR³ or S, wherein R³ is hydrogen, alkyl or aryl;
and Y¹ is C(=O), CH(OR'), or CH(R'), wherein R' is hydrogen or alkyl, said process comprising:
a) contacting a thioether of the formula:

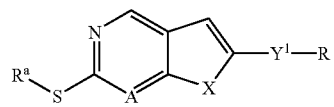

wherein A, R, X and Y¹ are as defined above;
and R$^a$ is alkyl or aryl, with an oxidizing agent to produce an alkylsulfone compound of the formula:

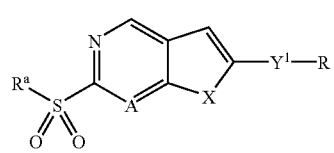

and b) contacting the alkylsulfone compound with an amine compound of the formula NHR¹R² to produce the compound of Formula IA wherein aryl and arylalkyl are each independently unsubstituted or substituted with 1, 2, or 3 substituents selected from the group alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl,—Y-heterocyclyl, —Y—OR$^p$, —Y—NR$^p$R$^q$, —Y—C(O)—R$^p$, —YS(O)$_{0-2}$R$^p$, —Y—N—S(O)$_{0-2}$R$^p$, —Y—S(O)₂NR$^p$R$^q$, —Y—N—C(O)NR$^p$R$^q$, where Y is a bond or C₁–C₃ alkylene, R$^p$ and R$^q$ are each independently selected from hydrogen, alkyl, haloalkyl, hydroxy, alkoxy, aryl, heteroaryl, cycloalkyl, and heterocyclyl, with the proviso that when the substituent is —YS(O)$_{1-2}$R$^p$ or —Y—N—S(O)²R$^p$ said R$^p$ is not hydrogen; heteroalkyl is unsubstituted or substituted with 1, 2, or 3 substituents selected from the group —OR$^a$, —NR$^h$R$^c$, and S(O)$_n$R$^d$ where n is an integer from 0 to 2, R$^a$, R$^b$, and R$^c$ are each independently hydrogen, acyl, alkyl, cycloalkyl, or cycloalkylalkyl, or R$^b$ and R$^c$ together with the N to which they are bound form heterocyclyl or heteroaryl, and R$^d$ is hydrogen, acyl, alkyl, cycloalkcyl, or cycloalkylalkyl when n is 0, and R$^d$ is alkyl, cycloalkyl, cycloalkylalkyl, amino, acylamino, monoalkylamino, or dialkylamino when n is 1 or 2; cycloalkyl is unsubstituted or substituted with 1, 2, or 3 substituents selected from the group alkyl, hydroxy, alkoxy, amino, monosubstituted amino, disubstituted amino, haloalkyl, halo, cyanoalkyl, oxo, heteroalkyl, heterocyclyl, hydroxyalkyl, —S(O)$_{0-2}$R', and —(X)$_n$—C(O)R", where X is O or NR", n is 0 or 1, R" is hydrogen, alkyl, haloalkyl, amino, monosubstituted amino, disubstituted amino, hydroxy, alkoxy, alkyl or optionally substituted phenyl, and R' is H or alkyl; heterocyclyl is unsubstituted or substituted with 1, 2, or 3 substituents selected from the group alkyl, hydroxy, hydroxyalkyl, alkoxy, heteroalkyl, and haloalkyl, and 0–2 ring carbon atoms are substituted with oxo; heteroaryl is unsubstituted or substituted with 1 or 2 substituents selected from the group alkyl, haloalkyl, heteroalkyl, heterocyclyl, halo, nitro, cyano, carboxy, acyl, -(alkylene)$_n$-COOR, and -(alkylene)$_n$—CONR$^a$R$^b$, where n is 0 or 1, R is hydrogen, alkyl, optionally substituted phenylalkyl, or optionally substituted heteroaralkyl, R$^a$ and R$^b$ are each independently hydrogen, alkyl, cycloalkyl, cycloalkylalkyl, hydroxyalkyl, aryl, or R$^a$ and R$^b$ together with the nitrogen atom to which they are attached form heterocyclyl or heteroaryl.

7. A process of producing a compound of Formula IB:

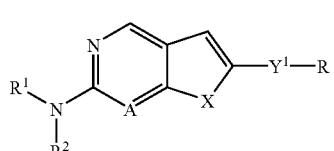

IB wherein A is N;
R is aryl or heteroaryl;
R¹ is hydrogen, alkyl or arylalkyl;
R² is alkyl, heteroalkyl, (R")₂NCO-alkylene- (where each R" is independently hydrogen or alkyl), cycloalkyl, heterocyclyl, aryl, or heteroaryl;
X is O, NR³ or S, wherein R³ is hydrogen, alkyl or aryl;

and $Y^1$ is O, NR', or $S(O)_n$, wherein n is 0, 1, or 2;
and R' is hydrogen or alkyl;
said process comprising contacting a compound of the formula:

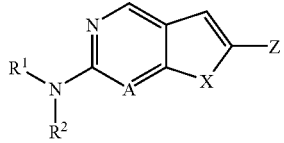

wherein A, X, $R^1$ and $R^2$ are as defined above;
and Z is halide, with an aromatic or heteroaromatic compound of the formula $HY^1$—R, optionally in the presence of a base, to produce the compound of Formula IB, where $Y^1$ is O, NR', or S, and when $Y^1$ is S, said process further comprising:
contacting the compound of Formula IB, where $Y^1$ is S with an oxidizing agent to produce the compound of Formula IB, where $Y^1$ is $S(O)_n$, where n is 1 or 2
wherein aryl and arylalkyl are each independently unsubstituted or substituted with 1, 2, or 3 substituents selected from the group alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl,—Y-heterocyclyl, —Y—$OR^p$, —Y—$NR^pR^q$, —Y—C(O)—$R^p$, —$YS(O)_{0-2}R^p$, —Y—N—$S(O)_{0-2}R^p$, —Y—$S(O)_2NR^pR^q$, —Y—N—C(O)$NR^pR^q$, where Y is a bond or $C_1$–$C_3$ alkylene, $R^p$ and $R^q$ are each independently selected from hydrogen, alkyl, haloalkyl, hydroxy, alkoxy, aryl, heteroaryl, cycloalkyl, and heterocyclyl, with the proviso that when the substituent is —$YS(O)_{1-2}R^p$ or —Y—N—S$(O)^2R^p$ said $R^p$ is not hydrogen; heteroalkyl is unsubstituted or substituted with 1, 2, or 3 substituents selected from the group —$OR^a$, —$NR^hR^c$, and S$(O)_nR^d$ where n is an integer from 0 to 2, $R^a$, $R^b$, and $R^c$ are each independently hydrogen, acyl, alkyl, cycloalkyl, or cycloalkylalkyl, or $R^b$ and $R^c$ together with the N to which they are bound form heterocyclyl or heteroaryl, and $R^d$ is hydrogen, acyl, alkyl, cycloalkyl, or cycloalkylalkyl when n is 0, and $R^d$ is alkyl, cycloalkyl, cycloalkylalkyl, amino, acylamino, monoalkylamino, or dialkylamino when n is 1 or 2; cycloalkyl is unsubstituted or substituted with 1, 2, or 3 substituents selected from the group alkyl, hydroxy, alkoxy, amino, monosubstituted amino, disubstituted amino, haloalkyl, halo, cyanoalkyl, oxo, heteroalkyl, heterocyclyl, hydroxyalkyl, —$S(O)_{0-2}R'$, and —$(X)_n$—C(O)R", where X is O or NR", n is 0 or 1, R" is hydrogen, alkyl, haloalkyl, amino, monosubstituted amino, disubstituted amino, hydroxy, alkoxy, alkyl or optionally substituted phenyl, and R' is H or alkyl; heterocyclyl is unsubstituted or substituted with 1, 2, or 3 substituents selected from the group alkyl, hydroxy, hydroxyalkyl, alkoxy, heteroalkyl, and haloalkyl, and 0–2 ring carbon atoms are substituted with oxo; heteroaryl is unsubstituted or substituted with 1 or 2 substituents selected from the group alkyl, haloalkyl, heteroalkyl, heterocyclyl, halo, nitro, cyano, carboxy, acyl, -(alkylene)$_n$-COOR, and -(alkylene)$_n$ —CON$R^aR^b$, where n is 0 or 1, R is hydrogen, alkyl, optionally substituted phenylalkyl, or optionally substituted heteroaralkyl, $R^a$ and $R^b$ are each independently hydrogen, alkyl, cycloalkyl, cycloalkylalkyl, hydroxyalkyl, aryl, or $R^a$ and $R^b$ together with the nitrogen atom to which they are attached form heterocyclyl or heteroaryl.

8. A process of producing a compound of Formula IC:

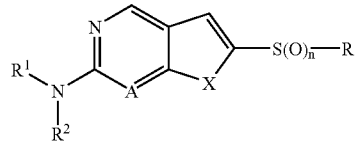

wherein n is 0, 1 or 2;
A is N;
R is aryl or heteroaryl;
$R^1$ is hydrogen, alkyl or arylalkyl;
$R^2$ is alkyl, heteroalkyl, (R")$_2$NCO-alkylene- (where each R" is independently hydrogen or alkyl), cycloalkyl, heterocyclyl, aryl, or heteroaryl;
and X is O, $NR^3$ or S, wherein $R^3$ is hydrogen, alkyl or aryl;
said process comprising: (a) contacting a compound of the formula:

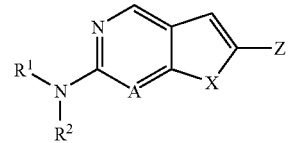

wherein $R^1$, $R^2$, A and X are as defined above;
and Z is halide, with an organometallic reagent;
and (b) adding an aryl or heteroaryl disulfide of the formula: R—S—S—R
to produce a thioether compound of the formula:

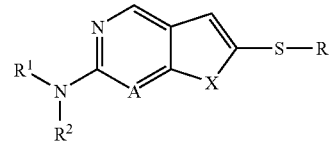

and when n is 1 or 2, said process further comprising: (c) contacting the thioether compound with an oxidizing agent to produce the compound of Formula IC where n is 1 or 2
wherein aryl and arylalkyl are each independently unsubstituted or substituted with 1, 2, or 3 substituents selected from the group alkyl, haloalkyl, halo, hydroxy, amino, haloalkoxy, cyano, nitro, heteroalkyl, methylenedioxy, ethylenedioxy, —Y-aryl, —Y-heteroaryl, —Y-cycloalkyl,—Y-heterocyclyl, —Y—$OR^p$, —Y—$NR^pR^q$, —Y—C(O)—$R^p$, —$YS(O)_{0-2}R^p$, —Y—N—$S(O)_{0-2}R^p$, —Y—$S(O)_2NR^pR^q$, —Y—N—C(O)$NR^pR^q$, where Y is a bond or $C_1$–$C_3$ alkylene, $R^p$ and $R^q$ are each independently selected from hydrogen, alkyl, haloalkyl, hydroxy, alkoxy, aryl, heteroaryl, cycloalkyl, and heterocyclyl, with the proviso that when the substituent is —$YS(O)_{1-2}R^p$ or —Y—N—S$(O)^2R^p$ said $R^p$ is not hydrogen; heteroalkyl is unsubstituted or substituted with 1, 2, or 3 substituents selected from the group —$OR^a$, —$NR^hR^c$, and S $(O)_nR^d$ where n is an integer from 0 to 2, $R^a$, $R^b$, and $R^c$ are each independently hydrogen, acyl, alkyl, cycloalkyl, or cycloalkylalkyl, or $R^b$ and $R^c$ together with the N to which they are bound form heterocyclyl or heteroaryl, and $R^d$ is hydrogen, acyl, alkyl, cycloalkyl, or cycloalkylalkyl when n is 0, and $R^d$ is alkyl, cycloalkyl, cycloalkylalkyl, amino, acylamino, monoalkylamino, or dialkylamino when n is 1 or 2; cycloalkyl is unsubstituted or substituted with 1, 2, or 3 substituents selected from the group alkyl, hydroxy, alkoxy, amino, monosubstituted amino, disubstituted amino, haloalkyl, halo, cyanoalkyl, oxo, heteroalkyl, heterocyclyl, hydroxyalkyl, —$S(O)_{0-2}R'$, and —$(X)_n$—C(O)R", where X is O or NR", n is 0 or 1, R" is hydrogen, alkyl, haloalkyl, amino, monosubstituted amino, disubstituted amino, hydroxy, alkoxy, alkyl or optionally substituted phenyl, and R' is H or alkyl; heterocyclyl is unsubstituted or substituted with 1, 2, or 3 substituents selected from the group alkyl, hydroxy, hydroxyalkyl, alkoxy, heteroalkyl, and haloalkyl, and 0–2 ring carbon atoms are substituted with oxo; heteroaryl is unsubstituted or substituted with 1 or 2 substituents selected from the group alkyl, haloalkyl, heteroalkyl, heterocyclyl, halo, nitro, cyano, carboxy, acyl, -(alkylene)$_n$-COOR, and -(alkylene)$_n$ —CONR$^a$R$^b$, where n is 0 or 1, R is hydrogen, alkyl, optionally substituted phenylalkyl, or optionally substituted heteroaralkyl, $R^a$ and $R^b$ are each independently hydrogen, alkyl, cycloalkyl, cycloalkylalkyl, hydroxyalkyl, aryl, or $R^a$ and $R^b$ together with the nitrogen atom to which they are attached form heterocyclyl or heteroaryl.

\* \* \* \* \*